United States Patent
Gnanadesikan et al.

(10) Patent No.: US 10,035,749 B2
(45) Date of Patent: Jul. 31, 2018

(54) PROCESS FOR MANUFACTURING ACRYLIC ACID, ACRYLONITRILE AND 1,4-BUTANEDIOL FROM 1,3-PROPANEDIOL

(71) Applicant: MYRIANT CORPORATION, Woburn, MA (US)

(72) Inventors: Vijay Gnanadesikan, Stonham, MA (US); Ramnik Singh, Winchester, MA (US); Rajesh Dasari, Lincoln, MA (US); Montgomery Alger, Hellertown, PA (US)

(73) Assignee: Myriant Corporation, Woburn, MA (US)

( * ) Notice: Subject to any disclaimer, the term of this patent is extended or adjusted under 35 U.S.C. 154(b) by 0 days.

(21) Appl. No.: 14/915,554

(22) PCT Filed: Sep. 3, 2014

(86) PCT No.: PCT/US2014/053933
§ 371 (c)(1),
(2) Date: Feb. 29, 2016

(87) PCT Pub. No.: WO2015/034948
PCT Pub. Date: Mar. 12, 2015

(65) Prior Publication Data
US 2016/0207865 A1    Jul. 21, 2016

Related U.S. Application Data

(60) Provisional application No. 61/873,328, filed on Sep. 3, 2013.

(51) Int. Cl.
C07C 51/27    (2006.01)
C07C 29/60    (2006.01)
(Continued)

(52) U.S. Cl.
CPC ............. *C07C 51/27* (2013.01); *C07C 29/44* (2013.01); *C07C 29/60* (2013.01); *C07C 51/16* (2013.01);
(Continued)

(58) Field of Classification Search
CPC ..... C07C 209/16; C07C 253/26; C07C 29/60; C07C 211/21; C07C 255/08; C07C 33/03;
(Continued)

(56) References Cited

U.S. PATENT DOCUMENTS 4,051,181 A * 9/1977 Murib ................ C07C 29/095
560/243
4,289,654 A * 9/1981 Bertolini ............ B01J 23/8878
502/244
(Continued)

FOREIGN PATENT DOCUMENTS

WO    2008021141 A2    2/2008
WO    2010115067 A2    10/2010
(Continued)

OTHER PUBLICATIONS

Segawa (Journal of Molecular Catalysis A: Chemical 310 (2009) 166-173).*
(Continued)

*Primary Examiner* — Valerie Rodriguez-Garcia
(74) *Attorney, Agent, or Firm* — Adam P. Lerner

(57) ABSTRACT

The present invention is in the field of producing bio-based commodity organic chemicals such as bio-acrylic acid, bio-acrylonitrile, and bio-1,4-butanediol using renewable carbon sources as feedstock. In the first stage of the present invention, bio-1,3-propanediol is derived from renewable carbon sources through microbial fermentation. In the sec-
(Continued)

ond stage of the present invention, bio-1,3-propanediol is converted into bio-acrylic acid or bio-acrylonitrile or bio-1,4-butanediol.

4 Claims, 15 Drawing Sheets

(51) Int. Cl.
  C07C 51/285     (2006.01)
  C07C 209/16     (2006.01)
  C07C 253/26     (2006.01)
  C07C 29/44      (2006.01)
  C07C 51/16      (2006.01)

(52) U.S. Cl.
  CPC .......... *C07C 51/285* (2013.01); *C07C 209/16* (2013.01); *C07C 253/26* (2013.01)

(58) Field of Classification Search
  CPC .......... C07C 29/44; C07C 51/16; C07C 51/27; C07C 51/285; C07C 57/04
  See application file for complete search history.

(56) References Cited

U.S. PATENT DOCUMENTS

| | | |
|---|---|---|
| 5,164,309 A | 11/1992 | Gottschalk |
| 5,254,467 A | 10/1993 | Kretschmann |
| 5,387,720 A | 2/1995 | Neher |
| 5,633,362 A | 5/1997 | Nagarajan |
| 5,686,276 A | 11/1997 | Laffend |
| 5,821,092 A | 10/1998 | Nagarajan |
| 6,013,494 A | 1/2000 | Nakamura |
| 6,361,983 B1 | 3/2002 | Ames |
| 6,428,767 B1 | 8/2002 | Burch |
| 6,479,716 B2 | 11/2002 | Hilary |
| 6,514,733 B1 | 2/2003 | Emptage |
| 7,135,309 B1 | 11/2006 | Laffend |
| 7,211,692 B2 | 5/2007 | Dieterle |
| 7,223,567 B2 | 5/2007 | Ka-Yiu |
| 7,259,280 B1* | 8/2007 | Kahn ............... C07C 29/60 568/903 |
| 7,371,558 B2 | 5/2008 | Cervin |
| 7,745,184 B2 | 6/2010 | Cervin |
| 7,858,350 B2 | 12/2010 | Burk |
| 7,947,483 B2 | 5/2011 | Burgard |
| 8,067,214 B2 | 11/2011 | Burk |
| 8,128,156 B2 | 3/2012 | Daab et al. |
| 8,129,169 B2 | 3/2012 | Van Dien |
| 8,129,170 B1 | 3/2012 | Van Dyk |
| 8,178,327 B2 | 5/2012 | Burk |
| 8,252,960 B2 | 8/2012 | Dubois |
| 8,357,520 B2 | 1/2013 | Burk |
| 8,530,210 B2 | 9/2013 | Sun |
| 8,597,918 B2 | 12/2013 | Clark |
| 8,715,971 B2 | 5/2014 | Pharkya |
| 2012/0202259 A1 | 8/2012 | Graber |
| 2012/0225461 A1 | 9/2012 | Dole |
| 2013/0130339 A1 | 5/2013 | Hermann |
| 2013/0157328 A1 | 6/2013 | Ozmeral |
| 2015/0266005 A1* | 9/2015 | Lin .................. C07C 45/38 560/207 |

FOREIGN PATENT DOCUMENTS

| | | |
|---|---|---|
| WO | 2011063055 A2 | 5/2011 |
| WO | 2011063157 A2 | 5/2011 |
| WO | 2011082378 A2 | 7/2011 |
| WO | 2011123154 A2 | 10/2011 |
| WO | 2011130725 A2 | 10/2011 |
| WO | 2012018699 A2 | 2/2012 |
| WO | 2012033845 A2 | 3/2012 |
| WO | 2012082720 A2 | 6/2012 |
| WO | 2012015770 A2 | 1/2013 |
| WO | 2013052717 A2 | 4/2013 |
| WO | 2013134385 A2 | 9/2013 |

OTHER PUBLICATIONS

Bioprocessing Technologies in Biorefinery for Sustainable Production of Fuels, Chemicals, and Polymers (First Edition, Edited by Shang-Tian Yang, Heshan E. El-Enshasy, and Nuttha Thongchul; 2013 John Wiley & Sons, p. 399-413, May 2013).*
Huang (Catal. Lett. (2009) 131:312-320).*
Miklos (Polyhedron, 13(3), 445-449 (1994)—abstract only).*
Burk, M. J. "Sustainable production of industrial chemicals from sugars" International Sugar Journal. 2010, pp. 30-35, vol. 112.
Da Silva, G. P. et al. "Glycerol: A promising and abundant carbon source for industrial microbiology" Biotechnology Advances. 2009, pp. 30-39, vol. 27.
Drochner, A. et al. "Acroleinoxidation to acrylica cid on MO/V/W-mixed oxide catalysts" Chemical Engineering Technology. 2014, pp. 398-408, vol. 37.
Gonen, C. et al. "Continuous production of 1,3-propanediol using waste glycerol with Clostridium beijernckii NRRL B-593 immobilized on glass beads and glass rings" Chemical and Biochemical Engineering Quarterly. 2013, pp. 227-234, vol. 27.
Gum, et al. "Selective conversion of glycerol to acrolein over supported nickel sulfate catalysts" Journal of Catalysis. 2013, pp. 93-102, vol. 301.
Industrial Biotechnology Review. "A conversation with Ellen Kullman" Industrial Biotechnology, 2014, pp. 247-250, vol. 10.
Jantama, K. et al. "Combination of metabolic engineering and metabolic evolution to develop nonrecombinant strains of *Escherichia coli* C that produce succinate and malate" Biotechnology and Biotechnology. 2008, pp. 1140-1153, vol. 99.
Jantama, K. et al "Eliminating side products and increasing succinate yields in engineered strains of *Escherichai coli* C" Biotechnology and Bioengineering. 2008 pp. 881-893, vol. 101.
McGrew, D. Getting to the point: Direct bio-based chemical production. Specialty Chemical Magazine. 2010. pp. 32-34, vol. 30.
Mendes, F. S. et al "1,3-Propanediol production in a two-step process fermentation from renewable feedstock" Applied Microbiology Biotechnology. 2011. pp. 519-527, vol. 92.
Nakamura, C.E. metabolic engineering for the microbial production of 1,3-propanediol. Current Opinion in Biotechnology. 2003. pp. 454-459, vol. 92.
Nielson, L. K. et al "Metabolic Engineering: From retrofitting to green field" Nature Chemical Biology. 2011. pp. 108-409, vol. 7.
Rao, G. S. et al "Vapour phase dehydration of glycerol to acrolein overNbOPO4 catalysts" Journal of Chemical Technology and Biotechnology. Published on line, Dec. 17, 2013.
Raynaud, C. et al Molecular characterization of the 1,3-propanediol (1,3-PD) operon of Clostridium butyicum. Proceedings of National Academy of Sciences USA. 2003. pp. 5010-5015. vol. 100.
Sato, S. et al "Selective dehydration of diols to allylic alcohols catalyzed by ceria" Catalytic Communication. 2003. pp. 77-81. vol. 4.
Sato, S. et al "Selective dehydration of alkanediol into unsaturated alcohols over rare earth oxide catalysts" ACS Catalysts. 2013. pp. 721-734. vol. 3.
Segawa, M. et al "Vapor-phase catalytic reactions of alcohols over bixbyite indium oxide" Journal of Molecular Catalysts A: Chemical 2009. pp. 166-173. vol. 310.
Soriano, M. D. et al "Tungsten-vanadium mixed oxide for the oxidehydration of glycerol into a acrylic acid" Green Chemistry. 2011, pp. 2954-2962. vol. 13.
Szymanowska-Powalowska, D. et al "An increasing of the efficiency of microbiological synthesis of 1,3-propanediol from crude glycerol by the concenration of biomass" Electronic Journal of Biotechnology. 2014. pp. 72-78. vol. 17.
Tang, X. et al "Microbial conversion of glycerol to 1,3-propanediol by an engineered strain of *Escherichia coli*" Applied and Environmental Microbiology. 2009. pp. 1628-1634. vol. 75.

(56) References Cited

OTHER PUBLICATIONS

Tahnsilp, S. et al "Preparation of supported POM catalysts for liquid phase oxydehydration of glycerol to acrylic acid" Journal of Molecular Catalysts A: Chemical. 2013. pp. 49-56. vol. 380.

Ulgen A. et al "Conversion of glycerol to acrolein in the presence of WO3/TiO2 catalysts" Applied Catalysis A: General, 2011. pp. 34-38. vol. 400.

Vivier, L. et al "Ceria-based solid catalysts for organic chemistry" ChemSusChem. 2010, pp. 654-678. vol. 3.

Yim, H. et al "Metabolic engineering of *Escherichia coli* for direct production of 1,4-butanediol" Nature Chemical Biology. 2011. pp. 445-452. vol. 7.

Zeng, A. P. et al "Microbial production of diols as platform chemicals: Recent progresses" Current Opinion in Biotechnology. 2011. pp. 749-757. vol. 22.

Diaz, E. et al "Homogenouos oxidation reactions of propanediols at low temperatures" ChemSusChem. 2010. pp. 1063-1070. vol. 3.

Wadley, D. C. et al "Lactic Acis conversion to 2,3-pentadione and acrylic acid over silica-supported sodium nitrate: Reaction optimization and identification of sodium lactate as the active catalyst" Journal of Catalysis. 1997. pp. 162-171. vol. 165.

\* cited by examiner

PROCESS FOR MANUFACTURING ACRYLIC ACID, ACRYLONITRILE AND 1,4-BUTANEDIOL FROM 1,3-PROPANEDIOL

CROSS-REFERENCE TO RELATED APPLICATION

The application is the U.S. national stage application of International Patent Application No. PCT/US2014/053933, filed on Sep. 3, 2014 which claims the priority of the U.S. Provisional Application Ser. No. 61/873,328 filed on Sep. 3, 2013.

FIELD OF THE INVENTION

This invention relates to a process for manufacturing bio-acrylic acid, bio-acrylonitrile and bio-1,4-butanediol from bio-1,3-propanediol through simple one or two step chemical processes. The bio-1,3-propanediol used as the starting materials in the present invention, is obtained from one or other renewable carbon resources through microbial fermentation.

BACKGROUND OF THE INVENTION

There has been a growing interest in manufacturing commodity chemicals using renewable biological materials as feedstock. For example, biocatalysts have been developed to manufacture succinic acid, lactic acid, 3-hydroxypropionic acid, 1,3-propanediol, 1,4-butanediol and butanol using biological feedstock such as glucose, glycerol, sucrose and cellulosic hydrolysates. The commodity chemicals thus derived from biological materials can be used in a number chemical industries as a drop-in substitute for raw materials currently derived from petrochemical feedstock. The present invention provides novel methods for manufacturing bio-acrylic acid, bio-1,4-butanediol and bio-acrylonitrile using biomass-derived 1,3-propanediol which is currently manufactured at commercial scale in a cost-effective way using biological feedstock.

Acrylic acid and its esters are important commodity chemicals used in the production of polyacrylic esters, elastomers, superabsorbent polymers, floor polishes, adhesives, paints, and the like. Historically, acrylic acid has been produced by hydroxycarboxylation of acetylene. This method utilizes nickel carbonyl and high pressure carbon monoxide, both of which are expensive and considered environmentally unfriendly. Other methods, e.g., those utilizing ethenone and ethylene cyanohydrins as the raw materials, generally have the same pitfalls. BASF (Germany), Dow Chemicals (USA), Arkema (France), and Nippon Shokubai (Japan) are using propylene as the raw material for acrylic acid manufacturing.

There is a growing interest in manufacturing bio-acrylic acid using renewable resources. Lactic acid and 3-hydroxypropionic acid derived from biological fermentation of carbohydrates are considered to be ideal raw material for manufacturing acrylic acid through vapor-phase dehydration reaction mediated by chemical catalysts. The process conditions for deriving acrylic acid from lactic acid and 3-hydroxypropionic acid are being worked out and are far from reaching commercial scale manufacturing. Dow Chemicals has partnered with OPXBio to develop bioacrylic acid using 3-hydroxypropionic acid derived from the fermentation of sugars. BASF is also collaborating with Novozymes A/S and Cargill Inc. to manufacture bio-acrylic acid using fermentation-derived 3-hydroxypropionic acid as the starting material. Myriant Corporation and Procter & Gamble are also independently developing a process involving vapor phase dehydroxylation of biomass-derived lactic acid. Metabolix is attempting to manufacture bio-acrylic acid using its FAST (fast acting selective thermolysis) process. Genomatica has developed a novel method for bio-acrylic acid manufacturing using fumaric acid derived from fermentation process. Genomatica technology utilizes ethylene and fumaric acid to perform metathesis reaction to produce acrylic acid. These various current approaches for manufacturing bio-acrylic acid are not yet cost competitive to propylene-based acrylic acid manufacturing and involves recovery steps which is expected to contribute to high capital cost and operational cost. Thus there is a need for additional cost-effective methods for manufacturing biomass-derived acrylic acid and its esters at commercial scale. This present invention provides a simple two-step scalable process for manufacturing bio-acrylic acid using biomass-derived 1,3-propanediol.

Succinic acid derived from biological feedstock such as glucose, sucrose, glycerol and cellulosic hydrolysates is being considered as a suitable drop-in feedstock in the manufacture of useful industrial chemicals such as 1,4-butanediol (BDO), gamma-butryolactone (GBL) and tetrahydrofuran (THF). BDO is currently used as an industrial solvent in the manufacture of plastics and polyesters and is a precursor to useful chemicals like GBL and THF. It is a protic polar solvent, which is miscible with water. The global market for BDO is about 3 billion pounds per year, almost exclusively produced from petrochemical processes. GBL is suitable as a solvent, to replace environmentally harmful chlorinated solvents, in the preparation of pyrrolidones used as a raw material in the manufacture of herbicides, rubber additives, and pharmaceuticals, and in the production of biodegradable polymers. THF is an aprotic, water miscible solvent used in organic chemistry. It is also widely used in the production of resins and polymers.

The typical process to produce BDO starts from petrochemical-derived acetylene which is reacted with formaldehyde using Reppe chemistry. The resulting 1,4-butynediol is then hydrogenated to form BDO. There are several other chemical routes to synthesize BDO, but one of the most economical routes starts from butane as a raw material. First, butane is oxidized to produce maleic anhydride. Then maleic anhydride can be converted to BDO via the BP/Lurgi Geminox process or the Davy Technology Process. The former process recovers maleic anhydride as maleic acid and performs liquid-phase hydrogenation to produce a mixture of BDO with THF and/or GBL. In the Davy Technology Process, maleic anhydride is esterified to dimethyl maleate, which is then vaporized and fed to a vapor-phase hydrogenation system to produce dimethyl succinate. Dimethyl succinate undergoes hydrogenolysis reaction to produce GBL and BDO, which can be further converted into THF. These products are separated by distillation and methanol is recycled back to the esterification reactor.

The conventional process for producing BDO, GBL, and THF is not a sustainable process, since the raw material is derived from petrochemical feedstock. One of the possible pathways to produce bio-BDO is by esterifying the bio-succinic acid to dialkyl succinate, followed by a hydrogenation step to produce BDO, GBL, and THF. Another approach that has been followed to manufacture bio-BDO is to engineer a microbial organism capable of producing bio-BDO as a fermentation product (Burk, *Int. Sugar J.* 112, 1333 (2010); McGrew, *Specialty Chem Mag.* July 2010, pp 32-34; Yim et al., *Nature Chem Bio.* 7, 445 (2011)). U.S. Pat.

Nos. 7,858,350 and 8,129,156 provides microorganism for the production of 1,4-butanediol. U.S. Pat. No. 8,067,214 provides composition and methods for the biosynthesis of 1,4-butanediol and its precursors. U.S. Pat. No. 8,129,169 provides microorganisms for the production of 1,4-butanediol and related methods. U.S. Pat. No. 7,947,483 provides methods and organisms for the growth coupled production of 1,4-butanediol. U.S. Pat. No. 8,715,971 provides microorganisms and method for the coproduction of isopropanal and 1,4-butanediol. U.S. Pat. No. 8,530,210 provides microorganisms and methods for the coproduction of 1,4-butanediol and gamma-butryolactone. U.S. Pat. No. 8,597,918 provides a process for separating 1,4-butanediol from a fermentation broth. The present invention provides yet another novel and cost-effective method for producing bio-BDO using biomass-derived 1,3-propanediol as the starting material.

Acrylonitrile is yet another commodity chemical that can be manufactured according to the present invention using biomass-derived 1,3-propanediol as the starting material. Acrylonitrile is widely used in large quantities in a number of commercial products and processes, notably in clothing and plastics. It is used in the production of many different synthetic polymers (ABS—Acrylonitrile butadiene styrene; ASA—Acrylonitrile styrene acrylate; NBR—Nitrile butadiene rubber; and SAN—Styrene acrylonitrile). ABS is used in everything from children's LEGO toys to golf club heads and car parts. NBR is probably most identifiable in non-latex gloves, but is also used in synthetic leather, gaskets, and seals. SAN is most commonly found in kitchen products because of its higher tolerance for heat. Furthermore, acrylonitrile is industrially used as a starting reagent for the production of acrylic acid. Currently acrylonitrile is obtained from propylene through oxidation reaction using bismuthphosphomolybdate catalyst. Propylene used in the manufacture of acrylonitrile is derived as a byproduct of petroleum and natural gas refining. There is a need to produce bio-based acrylonitrile from renewable resources. The present invention provides a novel method for manufacturing bio-acrylonitrile using biomass-derived 1,3-propanediol as the starting material.

SUMMARY OF THE INVENTION

This present invention provides a process for manufacturing bio-acrylic acid, bio-acrylonitrile and bio-1,4-butanediol from bio-1,3-propanediol through one or two simple chemical reactions. Bio-1,3-propanediol suitable for this invention is derived from renewable carbon resources through fermentation using a biocatalyst.

In one embodiment of the present invention bio-acrylic acid is derived from a renewable carbon source through a process carried out in two stages. In the first stage of the process according to the present invention, suitable biocatalysts are used to produce bio-1,3-propanediol through biological fermentation. In the second stage of the present invention, biomass-derived 1,3-propanediol is converted into acrylic acid through a two-step chemical reaction. In the first step of this chemical conversion process, bio-1,3-propanediol is subjected to catalytic dehydration reaction leading to production of bio-allyl alcohol which in turn is oxidized to yield bio-acrylic acid. Bio-1,3-propanediol used in this invention is obtained from renewable carbon sources including, among other things, glucose, sucrose, glycerol and cellulosic hydrolysates through fermentation involving biocatalysts.

In another aspect of this embodiment for the production of bio-acrylic acid using bio-1,3-propanediol as the starting material, a two-stage process with bio-acrolein as an intermediate is provided. In the first stage of this process biomass-derived 1,3-propanediol is obtained from renewable carbon resources through fermentation involving biocatalysts. In the next stage of the present invention, biomass-derived, 1,3-propanediol is subjected to catalytic dehydration reaction under mild oxidizing condition to yield a mixture of bio-allyl alcohol and bio-acrolein which are subsequently fully-oxidized to yield bio-acrylic acid.

In another aspect of this embodiment, biomass-derived 1,3-propanediol reacts with oxygen via homogeneous pathways at 400°-500° K. During this homogeneous oxidation reaction, 1,3-propanediol undergoes dehydration and oxidative dehydrogenation to form, almost exclusively, acrolein (ca. 90% selectivity). The acrolein thus formed as a result of homogeneous oxidation reaction is subjected to further oxidation in the presence of heterogeneous catalyst to yield acrylic acid.

In yet another aspect of this embodiment, bio-1,3-propanediol is subjected to single step oxydehydration reaction to yield acrylic acid.

In another embodiment of the present invention, a process for the production of bio-acrylonitrile is provided. In one aspect of this embodiment, biomass-derived 1,3-propanediol is subjected to dehydration reaction to yield allyl alcohol which in turn is subjected to amination reaction to yield bio-allyl amine. In the next stage of this process, bio-allyl amine is subjected to an oxidation reaction to yield bio-acrylonitrile. In another aspect of this embodiment, bio-allyl alcohol is subjected to a single step reaction involving ammoxidation catalyst to yield acrylonitrile.

In yet another embodiment of the present invention, a two-stage process for the production of bio-1,4-butanediol from renewable carbon resources is provided. In the first stage of this process, 1,3-propanediol is derived from carbon sources including glucose, sucrose, glycerol and cellulosic hydrolysates using a biocatalyst. In the second stage of this process, biomass-derived 1,3-propanediol is subjected to a dehydration reaction leading to the production of bio-allyl alcohol, which in turn is subjected to hydroformylation and a hydrogenation reaction to yield bio-1,4-butanediol and 2-methyl-1,3-propanediol.

According to another embodiment of the present invention, bio-allyl alcohol derived from bio-1,3-propanediol is used as drop-in chemical intermediate in the conventional acrylic acid manufacturing plant designed to utilize propylene feedstock leading to the production of bio-acrylic acid. In another aspect of the present invention, bio-allyl alcohol derived from bio-1,3-propanediol is used as a drop-in chemical intermediate in the conventional 1,4-butanediol manufacturing plant designed to utilize propylene oxide feedstock leading to the production of bio-1,4-butanediol.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE PREFERRED EMBODIMENTS

Figure 1:
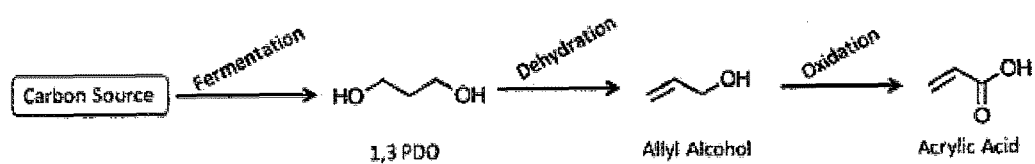
FIG. 1. Bio-Acrylic acid and bio-acrylonitrile production from biomass-derived 1,3-propanediol through allyl alcohol. The 1,3-propanediol useful for the present invention is derived from renewable carbon sources including glucose, sucrose, glycerol and cellulosic hydrolysates through fermentation involving biocatalysts. Biomass-derived 1,3-propanediol is subjected to dehydration reaction to yield bio-allyl alcohol. Upon oxidation reaction, bio-allyl alcohol yields bio-acrylic acid.

The present invention provides methods for producing bio-acrylic acid, bio-acrylonitrile and bio-1,4-butanediol using bio-1,3-propanediol as the starting material. The term "bio" placed as a prefix to each of the commodity chemicals of the present invention means that the carbon atoms in each of those commodity chemicals are derived from renewable materials that are produced naturally in plants. The biomass-derived chemicals of the present invention, including bio-1,3-propanediol, bio-acrylonitrile, bio-acrylic acid and bio-1,4 butanediol have been traditionally manufactured from petroleum feedstock. The prefix "bio" is used in this patent specification for the purpose of distinguishing the products obtained by using the manufacturing process according to the present invention from similar products derived from the traditional manufacturing process involving petroleum feedstock.

The bio-based commodity chemicals manufactured according to the present invention can be distinguished from the similar commodity chemicals manufactured following the traditional methods involving petroleum feedstock on the basis of their carbon 14 content following the method ASTM-D6866 provided by American Society of Testing and Materials. Cosmic radiation produces $^{14}C$ ("radiocarbon") in the stratosphere by neutron bombardment of nitrogen. $^{14}C$ atoms combine with oxygen atom in the atmosphere to form heavy $^{14}CO_2$, which, except in the radioactive decay, is indistinguishable from the ordinary carbon dioxide. $CO_2$ concentration and the $^{14}C/^{12}C$ ratio is homogeneous over the globe and because it is used by the plants, the ratio $^{14}C/^{12}C$ is retained by the biomass while the content of $^{14}C$ in the fossil materials, originally derived from photosynthetic energy conversion, has decayed due to its short half-life of 5730 years. By means of analyzing the ratio of $^{14}C$ to $^{12}C$, it is possible to determine ratio of fossil fuel derived carbon to biomass-derived carbon. International Patent Application Publication No. WO2009/155085 A2 and U.S. Pat. No. 6,428,767 provide details about the use of use of ASTM-D6866 method for determining percent of biomass-derived carbon content in a chemical composition. International Patent Application Publication No. WO2009/155085 A2 provides isocyanate and polyisocyanate compositions comprising more than 10 percent of carbon derived from renewable biomass resources. U.S. Pat. No. 6,428,767 provides a new polypropylene terephthalate composition. This new polypropylene terephthalate is comprised of 1,3-propanediol and terephthalate. The 1,3-propanediol used in this composition is produced by the bioconversion of a fermentable carbon source, preferably glucose. The resulting polypropylene terephthalate is distinguished from a similar polymer produced using petrochemical feedstock on the basis of dual carbon-isotopic fingerprinting which indicates the source and the age of the carbon. The details related carbon dating disclosed in the U.S. Pat. No. 6,428,767 is incorporated herein by reference. An application note from Perkin Elmer entitled "Differentiation Between Fossil and Biofuels by Liquid Scintillation Beta Spectrometry—Direct Method" provides details about the methods involving ASTM Standard D6866.

The term "biomass" as used in the present invention refers to carbohydrates, sugars, glycerol and lignocellulosic materials derived from renewable plant resources which can be used in the fermentative production of commodity chemicals including 1,3-propanediol.

The term "dehydration" or "dehydroxylation" as used in the present invention refers to a chemical reaction that removes one or more water molecules from a chemical compound.

The term "hydration" or "hydroxylation' as used in the present invention refers to a chemical reaction that adds one or more water molecules to a chemical compound.

The term "oxidation" as used in the present invention refers to the addition of an oxygen atom to a chemical compound or removal of hydrogen atoms.

The term "hydroformylation" as used in the present invention refers to the addition of a hydrogen atom and carbon monoxide to a chemical compound.

The term "hydrogenation" as used in this invention refers to the addition of a hydrogen atom to a chemical compound.

The term "oxydehydration" as used in the present invention refers to a chemical reaction involving both dehydration and oxidation reaction.

The term "ammoxidation" or "amino-oxidation" as used in the present invention refers to a chemical reaction involving both amination and oxidation reactions.

The term "biocatalyst" as used in the present invention refers to a microbial organism that has been genetically modified to produce one or other industrially useful chemicals using biomass-derived sugars in a fermentative process.

The term "conversion" as used the present invention refers to the percent of the reactant that has been used in a chemical conversion process. For example, when a compound "A" is converted into another compound "B" in a chemical reaction, the conversion efficiency of the chemical reaction is obtained using the Equation (1).

$$\text{(Moles of compound "B" formed/Moles of compound "A" originally present)} \times 100 \quad \text{Equation (1)}$$

The term "selectivity" as used in the present invention refers to the percentage of a particular product formed in a chemical reaction among the plurality of the products formed in that particular chemical reaction. For example, when a chemical reaction yields products "A", "B", "C" and "D", the selectivity of that chemical reaction to the product "A" is obtained using the Equation (2).

$$\text{(Moles of compound "A" formed/Moles of compounds "A", "B", "C", and "D" formed)} \times 100 \quad \text{Equation (2)}$$

A large number of carbohydrate materials derived from natural plant resources can be used as a feedstock in conjunction with the fermentative production of 1,3-propanediol used as a starting material in the present invention. The cereal crops like maize and wheat contain starch as their primary carbohydrate material and require pre-hydrolysis step prior to sugar fermentation. The sugar crops such as sugar cane and sugar beet contain readily fermentable sucrose. The cereal crops and sugar crops are considered as the first generation feedstock in the manufacture of renewable chemicals including 1,3-propanediol. However, a continued use of first generation feedstock in the production of renewable chemicals is not sustainable in the long run due to the concerns about human food security and land-use issues. There has been effort to develop second generation feedstock which would reduce the cost of production of renewable chemicals further.

The term second generation feedstock as used in this present invention refers to non-food lignocellulosic biomass. Lignocellulose is the most abundant form of renewable carbon on the earth. Lignocellulosic biomass available for renewable chemical feedstock manufacturing can be grouped under two categories. (1) Biowaste material including straws, corn residues (stover, fibers, and cobs), woody wastes/chipping, forestry residues, old paper/cardboard, bagasse, spent grain, municipal solid waste, agricultural residues (oil seed pulp, sugar beet pulp, etc.); (2) Energy crops including but not limited to short rotation crops such as basket willow (*Salix viminalis*), energy grass (*Miscanthus giganteus*), alfalfa (*Medicago sativa*), switch grass (*Panicum vigratum*), reed canary grass (*Arundo donax*), rye grass etc.

A recent report from U.S. Department of Energy entitled "U.S. Billion-Ton Update—Biomass supply for a Bioenergy and Bioproducts Industry" has projected that the US would have between 1.1 and 1.6 billion tons of sustainable biomass available for industrial bio-processing by 2030. The challenge in front of the bio-processing industry is to recover the fermentable sugars from the lignocellulosic biomass in a cost-effective way.

The cost of fermentation process for producing industrial chemicals can be significantly reduced by using lignocellulosic biomass as the source of carbon in the fermentation process. Lignocellulosic biomass consists of roughly 40-50% of hexose sugars and 10-30% of pentose sugars. The hexose sugars are known in the art as C6 sugars. The pentose sugars are known in the art as C5 sugars. When hydrolyzed, the lignocellulosic materials yield a mixture of sugars that includes glucose, xylose, arabinose, mannose and galactose. However, most of the biocatalysts currently used in the fermentation processes for the production of industrial chemicals utilize pure glucose as a source of carbon for their growth and metabolism. For example, the *E. coli* strain useful in the fermentative production of lactic acid described in U.S. Pat. No. 7,223,567 uses a rich medium supplemented with glucose as the source of carbon. The *E. coli* strain KJ122 useful for the production of succinic acid described by Jantama et al (2008a; 2008b) and in the published PCT Patent Application Nos. WO/2008/021141A2 and WO2010/115067A2 and the U.S. Pat. No. 8,691,539 requires a minimal medium supplemented with glucose.

The ability of the microorganism to use multiple sugars simultaneously is limited by the existence of certain biochemical regulatory systems. These biochemical regulatory systems within the microbial cells have a genetic basis. At present the industrial microorganisms are grown in a medium containing glucose or sucrose as the source of carbon. The presence of glucose in the growth medium suppresses the use of other sugars in *E. coli* and other species of industrial microorganisms. The consumption of other sugars such as xylose, a pentose sugar, by these microorganisms is initiated only after glucose in the growth medium has been fully consumed. This phenomenon related to carbon utilization in industrial microorganisms is referred to as catabolite repression or diauxic growth. A method to make the microorganisms co-utilize the different sugars such as C5 and C6 sugars through a relief of catabolite repression during the production of industrial chemicals in a commercial scale would be critical to lowering the cost of industrial chemicals produced by fermentation. Alternately, the C5 and C6 sugars from the lignocellulosic hydrolysate can be recovered in separate streams and subsequently fed to the biocatalysts at different times in order to maximize the use of both C5 and C6 fermentable sugars recovered from lignocellulosic biomass. Thus by means of utilizing both C5 and C6 sugars recovered from the lignocellulosic feedstock, the cost of manufacturing renewable chemical feedstock such as 1,3-propanediol using lignocellulosic biomass can further be reduced significantly.

Sucrose from cane and beet, glucose, whey containing lactose, maltose and dextrose from hydrolyzed starch, glycerol from biodiesel industry, sugars derived from the hydrolysis of variety of lignocellulosic materials and combinations thereof may be suitable for the fermentative production of 1,3-propanediol used as the starting material in the present invention. A microbial biocatalyst with ability to utilize both 6-carbon containing sugars such as glucose and 5-carbon containing sugars such as xylose simultaneously as provided in the U.S. Patent Application Publication No. 2012/0202259 is a preferred bacterial strain for developing a biocatalyst for the production of 1,3-propanediol.

Bio-1,3-propanediol derived from biological feedstock using one or other biocatalysts described in one or other United States Patent document cited in this specification is suitable for use in several chemical applications as described in the present invention. Bio-1,3-propanediol can be used as a substrate in the formulation of polyesters, polyethers, polyurethanes, adhesives, composites laminates, coatings and moldings. In addition, bio-1,3-propanediol is useful as a solvent or antifreeze agent. Bio-1,3-propanediol is currently used in the commercial manufacture of Sorona® Polymer with acceptable levels of softness, stretch & recovery, vibrant colors and printability qualities. The present invention introduce yet another use for bio-1,3-propanediol namely the manufacture of bio-acrylic acid, bio-acrylonitrile and bio-1,4-butanediol.

Biocatalysts suitable for the industrial scale fermentative production of bio-1,3-propanediol have been developed using metabolic engineering techniques and are currently in commercial use (Nakamura et al., *Curr. Opin Biotech.* 14, 454 (2003); Raynaud et al., *Proc. Natl. Aca. Sc. USA* 100, 5010 (2003); Mendes et al., *App. Microbio. Biotech.* 92, 519 (2011); Nielsen, *Nature Chem Biol.* 7, 408 (2011); Zeng et al., *Curr. Opin. Biotech.* 22, 749 (2011)). DuPont and Tate&Lyle formed a joint venture in 2004 for the commercial production of biomass derived 1,3-propanediol ("Bio-PDO") (IB Interview—A conversation with Ellen Kullman, *Ind Biotech.* 10, 247 (2014).

In certain embodiments of the metabolic engineering process useful in the construction of an *Escherichia coli* strain producing 1,3-propanediol, yeast genes for glycerol production and *Klebsiella pneumonia* genes for conversion of glycerol to 1,3-propanediol are introduced. U.S. Pat. No. 7,371,558 and U.S. Pat. No. 7,745,184 provide biocatalysts useful in the fermentative production of 1,3-propanediol. U.S. Pat. No. 6,479,716 provides a method for recovering 1,3-propanediol from fermentation broth. All of these United States patent references are incorporated herein by reference. Any one of these biocatalysts and the processes known in the art for the fermentative production of 1,3-propanediol can be used to obtain bio-1,3-propanediol useful as the starting material for manufacturing bio-acrylic acid, bio-acrylonitrile and bio-1,4-butanediol according to the present invention.

In another embodiment of the present invention, glycerol that is currently obtained as a byproduct from biodiesel industry can be used as a starting raw material for the production of acrylic acid, acrylonitrile, and 1,4-butanediol according to the present invention. In one aspect of the present invention, glycerol is used as a raw material in the synthesis of 1,3-propanediol. This can be achieved in two different ways. There are known methods for the chemical conversion of glycerol directly into 1,3-propanediol using either chemical catalysts or certain enzymes. Alternately, glycerol can be used as a carbon source for the fermentative production of 1,3-propanediol using certain biological catalysts.

Bacterial stains for the fermentative production of 1,3-propanediol using glycerol derived as a waste from biodiesel industry have been developed (da Silva et al., *Biotech. Adv.* 27, 30 (2009); Tang et al., *App. Env. Microbiol.* 75, 1628 (2009); Gonen et al., *Chem. Blochent Eng. Q.* 27, 227 (2013); Sznmanowska-Powalowska and Leja, *Elec. J. Biotech.* 17, 72 (2014). U.S. Pat. No. 5,164,309, U.S. Pat. No. 5,254,467, U.S. Pat. No. 5,633,362, and U.S. Pat. No. 5,821,092 provide biocatalysts useful in the fermentative production of 1,3-propanediol using glycerol as feedstock and all of these United States Patent documents have been incorporated herein by reference.

Figure 3:
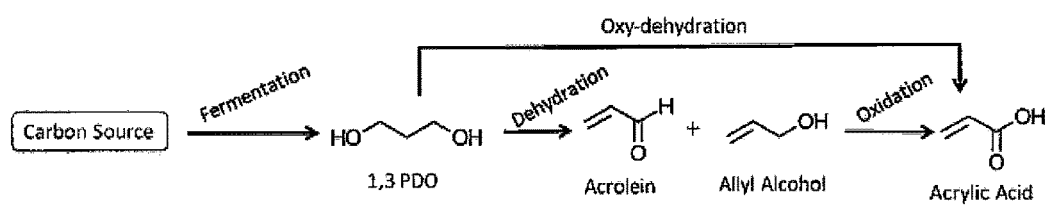
FIG. 3. Bio-acrylic acid production from biomass-derived 1,3-propanediol through bioacrolein as an intermediate. Biomass-derived, 1,3-propanediol is subjected to catalytic dehydration reaction under mild oxidizing condition to yield a mixture of bio-acrolein and bio-allyl alcohol which are subsequently fully-oxidized to yield bio-acrylic acid. Also shown in this figure is the pathway for oxydehydration reaction of 1,3-propanediol leading to the production of acrylic acid.

The manufacture of bio-acrylic acid from bio-1,3propanediol can be achieved through two different pathways each involving two different stages as illustrated in FIGS. 1 and 3. In the first stage of each of these processes for the production of acrylic acid, carbon sources such as glucose, sucrose, glycerol or cellulosic hydrolysates are subjected to fermentation involving biocatalysts leading to the production of bio-1,3-propanediol. In the second stage, both these pathways involve two distinct chemical reactions. In one pathway, bio-allyl alcohol is obtained as an intermediate through dehydration of bio-1,3-propanediol (FIG. 1). As mentioned above, bio-allyl alcohol can also be obtained directly from glycerol through catalyst-mediated dehydration and hydrogenation reaction. The bio-allyl alcohol thus obtained is subsequently subjected to an oxidation reaction to yield acrylic acid (FIG. 1). In another pathway for the production of bio-acrylic acid, biomass-derived 1,3-propanediol is subjected to a dehydration reaction under milder oxidizing conditions to yield a mixture of bio-acrolein and bio-allyl alcohol (FIG. 3). Bio-acrolein is also obtained directly from glycerol through catalyst mediated dehydration reaction. Bio-acrolein can also be obtained from bio-1,3-propanediol through homogeneous oxidation reaction without the use of any catalyst ((Diaz et al., *ChemSusChem* 3, 1063 (2010)). The bio-acrolein+bio-allyl alcohol mixture obtained as an intermediate is subsequently oxidized to yield bio-acrylic acid (FIG. 3).

Figure 12:
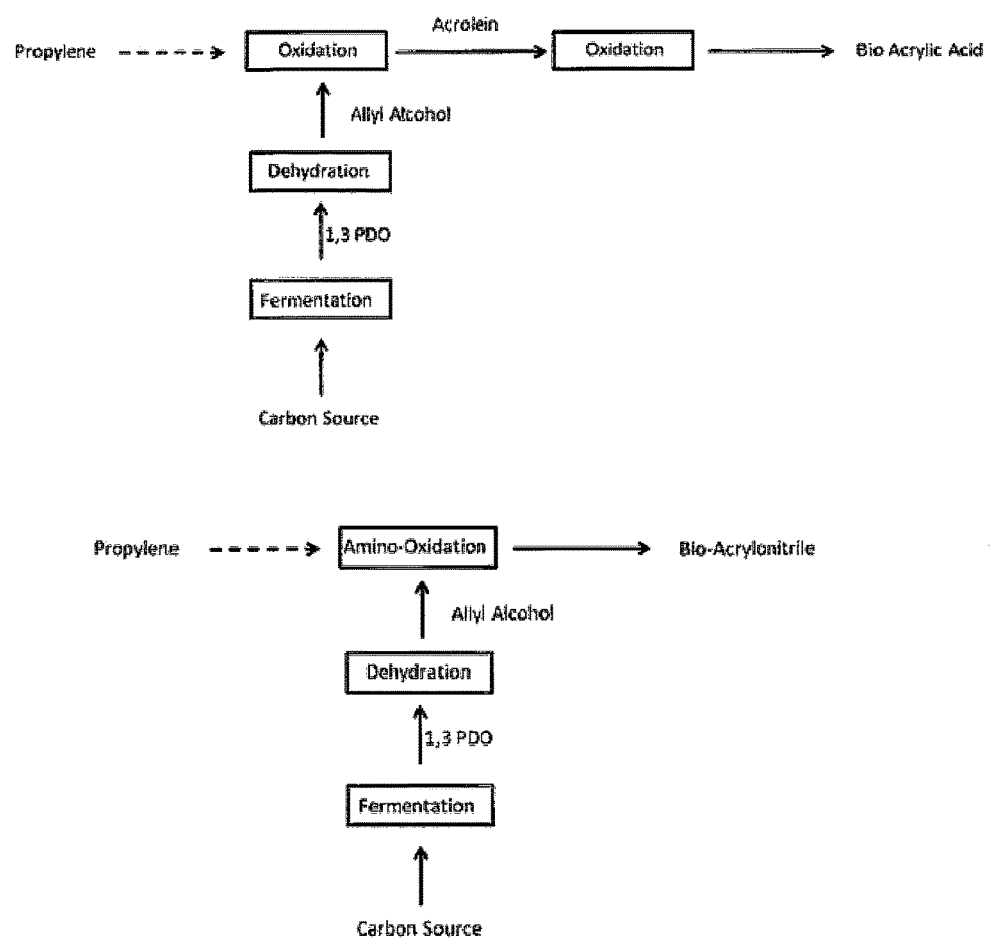
FIG. 12. Use of biomass-derived 1,3-propanediol as a drop-in chemical in the conventional process for the production of acrylic acid and acrylonitrile. In the conventional chemical process for the production of acrylic acid, propylene is oxidized to yield acrolein which in turn yields acrylic acid upon further oxidation. 1,3-propanediol is derived from biomass-derived carbon sources through fermentation process involving biocatalysts. Upon dehydration reaction, biomass-derived 1,3-propanediol yields bio-allyl alcohol which in turn is used as a drop-in chemical in the conventional process for the production of bio-acrylic acid involving acrolein as an intermediate. In the conventional chemical process for the production of acrylonitrile, propylene is subjected amino-oxidation reaction to yield acrylonitrile. In the conventional chemical refinery for acrylonitrile, one can use bio-allyl alcohol as a drop-in intermediate just before amino-oxidation reaction to produce bio-acrylonitrile.

In one aspect of the present invention, bio-allyl alcohol and bio-acrolein derived from bio-based 1,3-propanediol can be used as a drop-in chemical intermediate in the conventional petrochemical feedstock-based acrylic acid manufacturing plant (FIG. 12). In the conventional chemical process for the production of acrylic acid, propylene is oxidized to yield acrolein which in turn yields acrylic acid upon further oxidation. 1,3-propanediol is derived from biomass-derived carbon sources through fermentation process involving biocatalysts. Upon dehydration reaction, biomass-derived 1,3-propanediol yields bio-allyl alcohol which upon milder oxidation yields acrolein which in turn is used as a drop-in chemical in the conventional process for the production of bio-acrylic acid involving bio-acrolein as an intermediate.

Figure 2:
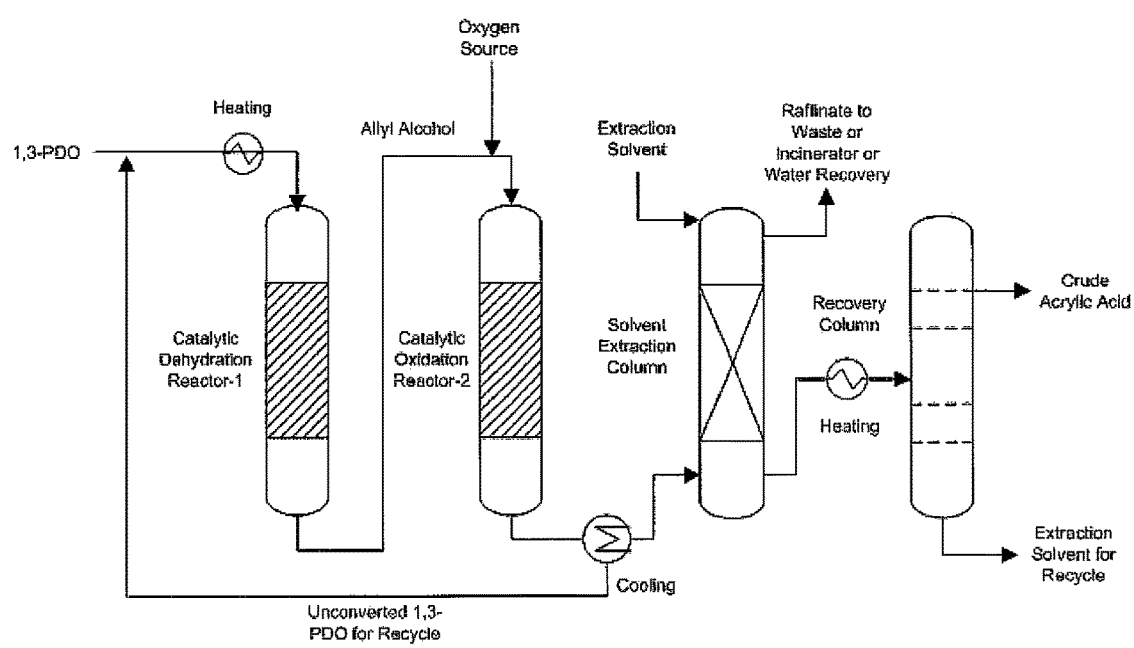
FIG. 2. Simplified process configuration for bio-acrylic production and purification. Biomass-derived 1,3-propanediol is subjected to sequential catalytic dehydration and catalytic oxidation reactions to yield bio-acrylic acid.

FIG. 2 provides simplified process configuration for bio-acrylic production and purification. In this configuration, biomass-derived 1,3-propanediol is subjected to sequential catalytic dehydration and catalytic oxidation reactions to yield bio-acrylic acid.

Figure 4:
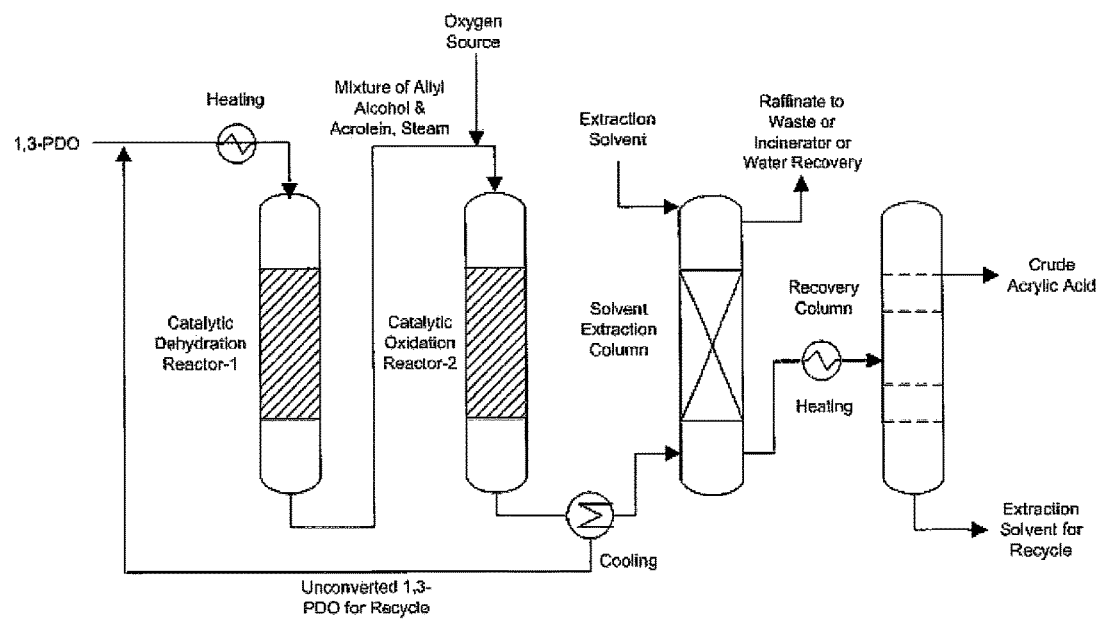
FIG. 4. Simplified process configuration for the bio-acrylic acid production and purification. Biomass-derived 1,3-propanediol is subjected to a catalytic dehydration reaction under mild oxidizing condition to yield a mixture of bio-acrolein and bio-allyl alcohol which are subsequently fully-oxidized to yield bio-acrylic acid.

FIG. 4 provides simplified process configuration for the bio-acrylic acid production and purification. Biomass-derived 1,3-propanediol is subjected to a catalytic dehydration reaction under milder oxidizing condition to yield a mixture of bio-acrolein and bio-allyl alcohol which are subsequently fully-oxidized to yield bio-acrylic acid.

Figure 5:
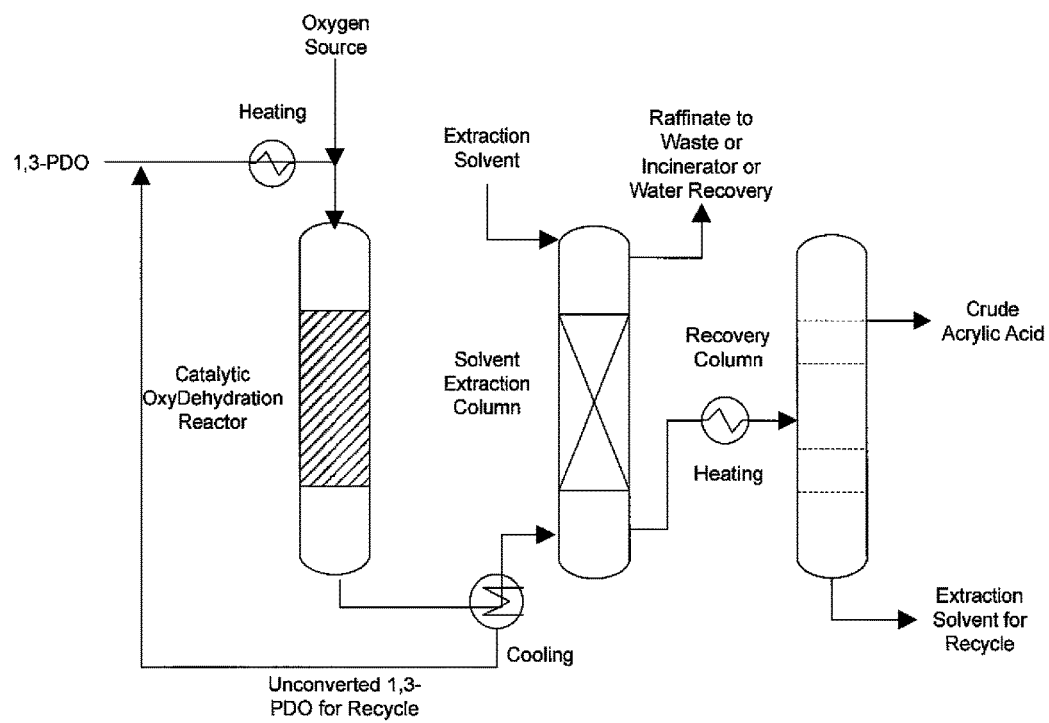
FIG. 5. Simplified process configuration for the bio-acrylic acid production and purification. Biomass-derived 1,3-propanediol is subjected to a single-step oxydehydration reaction to yield bio-acrylic acid.

FIG. 5 provides simplified process configuration for the bio-acrylic acid production and purification. Biomass-derived 1,3-propanediol is subjected to a single-step oxydehydration reaction to yield bio-acrylic acid.

Figure 6:
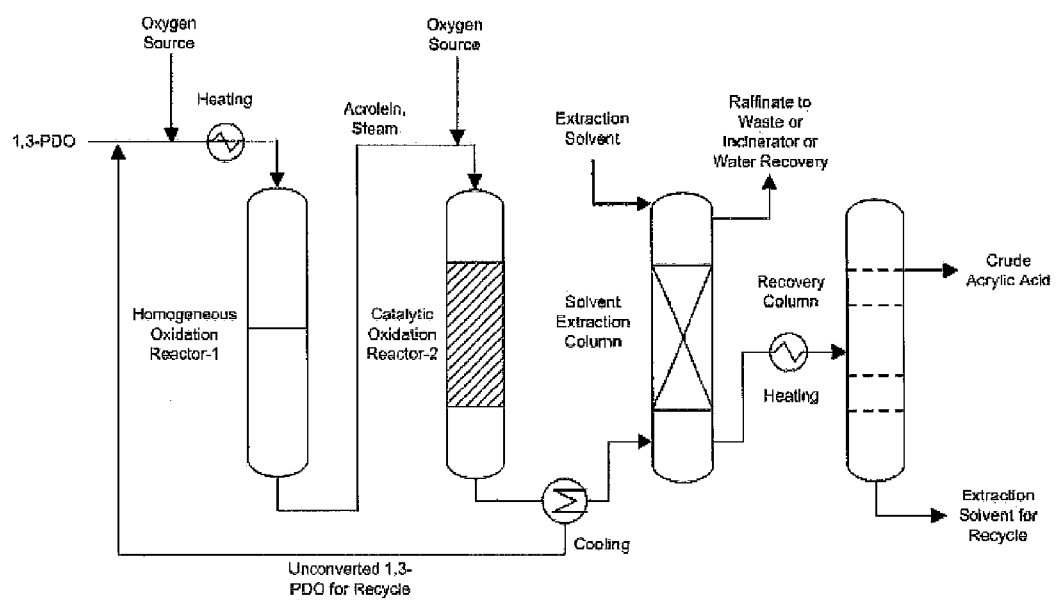
FIG. 6. Simplified process configuration for the bio-acrylic acid production and purification. Biomass-derived 1,3-propanediol is subjected homogeneous oxidation reaction, to form, almost exclusively, acrolein (ca. 90% selectivity). The acrolein thus formed as a result of homogeneous oxidation reaction is subjected to further oxidation in the presence of heterogeneous catalyst to yield acrylic acid.

FIG. 6 provides simplified process configuration for the bio-acrylic acid production and purification. Biomass-derived 1,3-propanediol is subjected homogeneous oxidation reaction, to form, almost exclusively, acrolein. The acrolein thus formed as a result of homogeneous oxidation reaction is subjected to further oxidation in the presence of heterogeneous catalyst to yield acrylic acid.

Catalytic Dehydration of bio-1,3-propanediol to Produce Allyl Alcohol:

Catalytic conversion of 1,3-propanediol into ally alcohol is well-known in the art and it is an endothermic reaction. Both the reactant (1,3-propanediol) and the product (allyl alcohol) are symmetrical alcohols and are stable compounds. The catalytic conversion of 1,3-propanediol into allyl alcohol results in minimal byproducts.

Synthesis of unsaturated alcohols in the vapor-phase catalytic dehydration of alkanediols over rare earth oxides has been reviewed (Sato et al., *ACS Catal.* 3, 721 (2013). Several rare earth oxides such as $CeO_2$, $Er_2O_3$ and $Yb_2O_3$ are known to be effective for the dehydration of diols, such as 1,3- and 1,4-butanediols, to produce unsaturated alcohols. Pure Ceria is used in several organic reactions such as the dehydration of alcohols. The redox and acid-base properties of Ceria activate complex organic molecules and selectively orient their transformation. $CeO_2$ catalyzes the dehydration of 1,3-diols into unsaturated alcohols (Vivier, L. and Duprez, D., *ChemSusChem* 3, 654 (2010)). Selective dehydration of diols to allylic alcohols catalyzed by Ceria has been reported. $CeO_2$ catalyzed the dehydration of 1,3-propanediol to 2-propen-1-ol (allyl alcohol) with the maximum selectivity of 98.9 mol % at 325° C. (Sato et al., *Catalysis Comm.* 4, 77 (2003). Indium oxide ($In_2O_3$) with cubic bixbyite structure is another catalyst useful for the vapor-phase catalytic dehydration of 1,3-propanediol to allyl alcohol in the temperature range of 300° C.-375° C. The selectivity to allyl alcohol in the dehydration reaction of 1,3-propanediol using $In_2O_3$ as a catalyst was higher than 90% with 2-propenal (acrolein) and acetaldehyde as the major byproducts (Segawa et al., *J. Mol. Cata. A: Chemical* 310, 166 (2009).

U.S. Pat. No. 7,259,280 has provided improvements of the cerium-containing catalysts in the production of allyl alcohol for the purpose of making this catalytic production of allyl alcohol commercially viable. The disclosures of U.S. Pat. No. 7,259,280 related to the cerium catalyst is incorporated herein by reference.

Many different type of cerium compounds including cerium oxides, hydroxides, nitrates, sulfates, halides and carboxylates, and mixtures thereof are useful for the dehydration of 1,3-propanediol to allyl alcohol. Cerium (IV) oxide, cerium (IV) hydroxide, cerium (IV) nitrate, cerium (IV) sulfate, cerium (IV) perchlorate, cerium (IV) acetate, cerium (IV) fluoride, cerium (IV) acetylacetate, cerium (IV)bromide, cerium (Ill) carbonate, cerium (III) chloride, and cerium (III) fluoride can be used in the preparation of the catalyst according to the present invention. It is necessary to convert any cerium compound to cerium oxide before the catalyst is used in the dehydration reaction.

The cerium catalyst according to the present invention is supported on a carrier selected from alumina, silica, titania, zirconia, magnesia, carbonate, magnesium, carbonate, silica-alumina, silica-titania, silica-zirconia and carbon. In general inorganic carriers are preferred and among the inorganic carriers, alumina is preferred while alpha alumina is most preferred. The surface area for the carrier is in the range of 0.5 to 30 $m^2/g$ and the particle size of the carrier is in the range of 0.1 micrometer to 10 micrometer. Cerium compounds are supported on the carrier by impregnation, ion exchange, adsorption or precipitation. When necessary the impregnated carrier may be calcined in the temperature range of 300° C. to 900° C.

For the purpose of improving the cerium oxide catalyst activity and/or selectivity, it is desirable to include other metal oxides such as aluminum, magnesium, calcium, barium, iron, cobalt, nickel, titanium, vanadium, scandium, yitrium, and the like and the resulting catalyst is referred as mixed metal oxide catalyst.

Cerium oxide based catalyst as well as the mixed metal oxide catalyst comprising cerium oxide are used in the temperature range of 250° C. to 450° C. and 1,3-propanediol is preferably used as a gas under reaction condition. An inert gas may be used as carrier gas with an inert gas to 1,3-propanediol ratio in the range of 1 to 100.

The catalyst is used either as a slurry or fluidized bed or a fixed bed; the catalytic process is performed in a continuous or semi-continuous or batch mode while the continuous flow mode is a preferred mode. Weight hourly space velocity (WHSV—grams of diol fed per gram of catalyst per hour) is in the range of 0.5 to 200 g/g catalyst/h.

Oxidation of Allyl Alcohol to Acrylic Acid:

Bio-allyl alcohol derived from dehydration reaction of bio-1,3-propanediol using cerium-based catalyst is subjected to catalytic oxidation reaction to obtain acrylic acid. While the cerium catalyzed dehydration reaction is an endothermic reaction, the oxidation of allyl alcohol into acrylic acid is an exothermic reaction. From the view point of atom economy, the two step conversion of 1,3-propanediol to acrylic acid has a 95% conversion efficiency. While the molecular weight of 1,3-propanediol is 76, the final end product acrylic acid has a molecular weight of 72.

The reaction conditions for the oxidation of allyl alcohol to produce acrylic acid is well known in the art and have been reported both in the scientific and patent literature. Direct oxidation of primary alcohols including allyl alcohol to the corresponding carboxylic acid has been performed with high efficiency at room temperature with anhydrous tert-butyl hydroperoxide in the presence of a catalytic amount of readily available CuCl under ligand free conditions in acetonitrile (Mannam & Sekar, *Tetra. Lett.* 49, 2457 (2008). Oxidation of $\alpha,\beta$-unsaturated alcohols with soluble manganese (IV) phosphate dissolve in 3M phosphoric acid has been reported (Jaky, *Polyhedron*, 13: 445(1994)). Japanese Patent Application Publication JP 2008-162907 provides a molybdenum vanadium catalyst for the preparation of acrylic acid from allyl alcohol by gas-phase catalytic oxidation. U.S. Pat. Nos. 4,051,181, 4,107,204 and 4,144,398 provide supported two-metal catalyst, one metal being palladium and the other metal being copper or silver. Palladium is used in the amount of 0.01 to 5 weight percent and the other metal is used in the range of 0.001 to 10 weight percent. Alumina, silica, silicon carbide, carbon, titania, zirconia, and zeolite can be used as support. The oxidation reaction is carried out in the vapor phase by passing the reaction mixture through the heated catalyst at a temperature of 125° C. to 320° C. Any one of the catalysts and the methods well-known in the art can be followed to carry out the oxidation of allyl alcohol to acrylic acid in an exothermic reaction. Under certain circumstances, acrolein may accumulate as major by-product which may further be subjected to an oxidation reaction to produce acrylic acid. The catalysts and the conditions for the conversion of acrolein to acrylic acid is well known in the art and can be followed to achieve total conversion of allyl alcohol into acrylic acid. Further detail about the conditions and the catalysts useful for the oxidation of acrolein to acrylic acid is provided in the sections below.

Catalytic Conversion of 1,3-propanediol into Acrylic Acid with Acrolein as an Intermediate:

In one embodiment of this part of the present invention, bio-1,3-propanediol is first subjected to a dehydration reaction under milder oxidizing conditions leading to the production of acrolein/allyl alcohol mixture as an intermediate. The acrolein/allyl alcohol mixture thus produced is subjected to an oxidation reaction in the second stage leading to the production of acrylic acid. In one aspect of this embodiment, dehydration reaction and oxidation reactions are carried out using two different heterogeneous catalysts. A number of catalysts have been reported in the literature for the dehydration of glycerol leading to the production of acrolein. Any one of those catalysts known to carry out the dehydration reaction with glycerol as a substrate can be used in the dehydration of 1,3-propanediol leading to the production of acrolein. Vapor phase dehydration of glycerol to acrolein over NbOPO4 catalysts has shown higher selectivity to acrolein with total conversion of glycerol (Rao et al., *J. Chem. Technol. Biotechnol* Article first published online: 17 Dec. 2013, DOI: 10.1002/jctb.4273). A maximum of 85% acrolein selectivity was achieved at nearly complete conversion of glycerol using novel $WO_3/TiO_2$ catalysts (Ulgen and Hoelderich, *App. Catalysis A: General* 400, 34 (2011)). Supported nickel sulfate has been proven to be an efficient catalyst for gas phase dehydration of glycerol to acrolein at 340° C. in the presence of oxygen (Gu et al., *J. Catalysis* 301, 93 (2013)). U.S. Pat. No. 5,387,720 discloses an acidic solid catalyst for producing acrolein by dehydration of glycerol in liquid phase or in gas phase at a temperature ranging up to 340° C. U.S. Pat. No. 8,252,960 discloses a catalyst useful in the preparation of acrolein by dehydration of glycerol comprising as a main component, at least one compound in which protons on a heteropolyacid are exchanged at least partially with at least one cation selected from elements belonging to Group 1 to Group 16 of the Periodic Table of Elements.

Once bio-acrolein+bio-allyl alcohol mixture is obtained from dehydration reaction involving 1,3-propanediol, the bio-acrolein+bio-allyl alcohol mixture is subjected to oxidation reaction to yield acrylic acid. Oxidation catalysts for the conversion of acrolein to acrylic acid are well known in the scientific as well as in the patent literature. Oxidation of acrolein to acrylic acid on Mo/V/W-mixed oxide catalyst has been studied (Drochner et al., *Chem. Eng. Tech.* 37, 398 (2014)). In the conventional process for manufacturing acrylic acid using propene as a feedstock, in the first step, propene is substantially oxidized using a heterogeneous catalyst to produce acrolein. In the second stage of this conventional process, the acrolein produced in the first stage is oxidized using a different type of heterogeneous catalyst to produce acrylic acid. The heterogeneous catalyst suitable for the oxidation of acrolein to acrylic acid in the propene-based acrylic acid manufacturing plant is referred as multi-metal oxides and these catalysts comprise the elements of Mo and V. U.S. Pat. No. 3,775,474, U.S. Pat. No. 3,954,855, U.S. Pat. No. 3,893,951, U.S. Pat. No. 4,339,355 and U.S. Pat. No. 7,211,692 provide details about the heterogeneous catalysts suitable for the oxidation of acrolein to acrylic acid. Any one of those catalysts known to be useful in conversion of acrolein to acrylic acid can be used in the present invention to oxidize bio-acrolein derived from bio-1,3-propanediol. Thus, with the extensive information available in the scientific and patent literature, a person skilled in the commercial manufacturing of acrylic acid will be well equipped to practice the bio-acrylic acid manufacturing process according to the present invention involving bio-acrolein as an intermediate In another aspect of this embodiment related to the conversion of bio-1,3-propanediol to acrylic acid through acrolein, a novel process called "oxydehydration" can be followed wherein the dehydration of the bio-1,3-propanediol to acrolein and the oxidation of acrolein to acrylic acid is carried out in a single stage. U.S. Pat. No. 7,910,771 is related to a method for producing acrylic acid in one step by an oxydehydration reaction of glycerol in the presence of molecular oxygen. The reaction is preferably carried out in gaseous phase in the presence of a suitable catalyst. A series of alumina-supported polyoxometalate ($Al_2O_3$-supported POM) catalysts was prepared by the impregnation method for the liquid phase catalytic oxydehydration of glycerol to acrylic acid in a batch reactor at low temperature (90° C.). Among the utilized $Al_2O_3$-supported POM catalysts, Si/W/ Al2O3 at 4 wt % loading exhibited the highest glycerol conversion of about 84% with a yield of acrylic acid of around 25% (Thanasli et al, *J. Mol. Catalysis A: Chemical* 380, 49 (2013)). One pot transformation of glycerol into acrylic acid, catalyzed by W/V mixed oxides, with hexagonal tungsten bronze structure has been tested (Soriano et al., *Green Chem.* 13, 2954 (2011)). The oxydehydration catalysts disclosed in the patent and scientific literature can be extended to achieve the conversion of bio-1,3-propanediol into bio-acrylic acid in one step as opposed to the two step conversion process described above in the other aspect of this embodiment of the present invention.

In yet another aspect of this embodiment for the conversion of bio-1,3-propanediol into acrylic acid through acrolein as an intermediate, the conversion from bio-1,3-propanediol into acrolein is achieved through oxidation process without the involvement of any heterogeneous catalyst. Recently it has been observed that in the presence of oxygen at elevated temperature of 400° C. and above, inside the homogenous reactor (reactor without any heterogeneous catalyst), there is a reaction chain leading to the formation of 3-hydroxypropanal which undergoes fast decomposition to yield acrolein. The selectivity for acrolein was found to be 90% at 400° C. and this value for acrolein selectivity decreased with further increase in temperature. It has also been shown that the effluent from the first homogeneous reactor can directly be fed into a second heterogeneous reactor containing $Mo_{0.61}V_{0.19}O_x$ catalyst. This process using a homogenous-heterogeneous reactors produces 91% acrylic acid and 9% acetic acid based on the conversion of 1,3-propanediol feed (Diaz et al., *ChemSusChem* 3, 1063 (2010)). It is well known that in the commercial acrylic acid manufacturing involving propene as the feed stock, acrolein as an intermediate and with two heterogeneous reactors, there is a problem of catalyst bed losing quality over a prolonged period of time of operation. In the case of a manufacturing process involving one homogeneous reactor and another heterogeneous reactor (FIG. 6), the problem of losing catalyst quality is reduced by half but it is not totally gone. We need to still address the problem of heterogeneous catalyst losing the quality over a prolonged period of time. One way that is generally followed to address this problem is to compensate lose of catalyst quality by increasing the operating temperature of the heterogeneous reactor after certain period of operation. Yet another way to compensate lose of quality of catalyst in the heterogeneous reactor is to conduct a gas mixture consisting of oxygen, inert gas and optionally steam through the heterogeneous reactor before increasing the operational temperature of the reactor. This practice of conducting a gas mixture through the heterogeneous reactor can be scheduled at pre-determined period of continuous operation such as after every 2000 hours of operation or after every 4000 hours of operation or after every 8000 hours of operation of the heterogeneous reactor.

Figure 7:
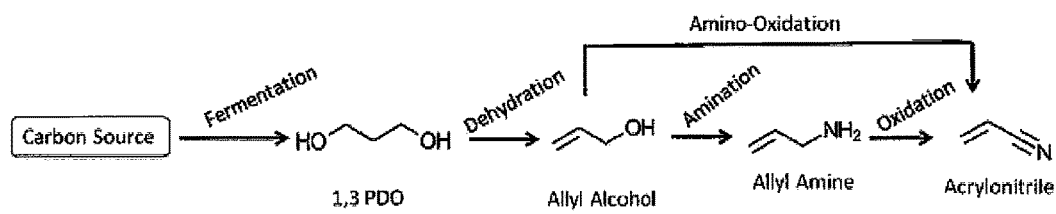
FIG. 7. Bio-acrylonitrile production from biomass-derived 1,3-propanediol through allyl alcohol intermediate. Biomass-derived 1,3-propanediol is subjected to dehydration reaction to yield bio-allyl alcohol. Bio-allyl alcohol thus produced is subjected to amination reaction to yield bio-allyl amine which in turn is subjected to an oxidation reaction to yield bio-acrylonitrile. Also shown in the figure is the single step ammoxidation reaction converting bio-ally alcohol into bio-acrylonitrile.
Figure 8:
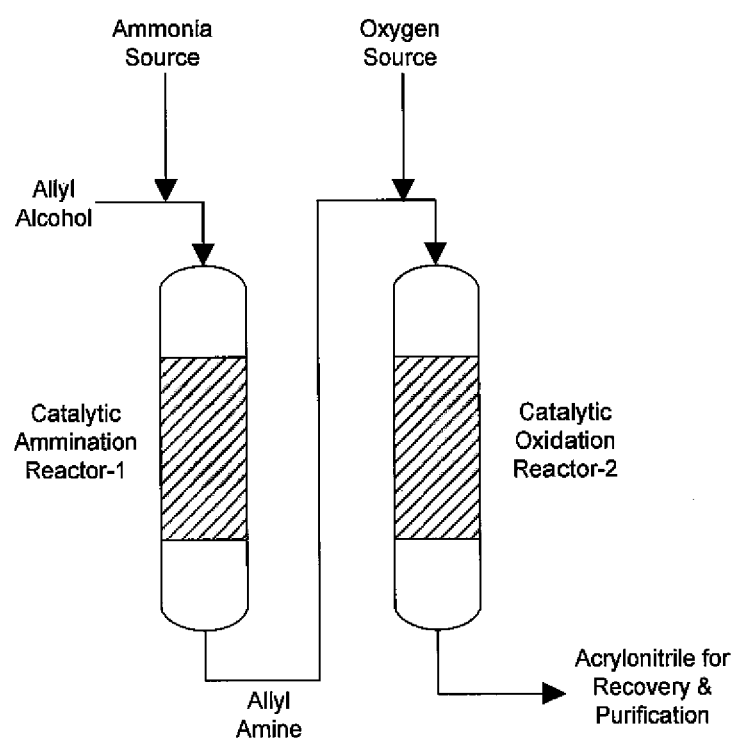
FIG. 8. Simplified process configuration for bio-acrylonitrile production. Biomass-derived 1,3-propanediol is subjected to catalytic dehydration reaction to yield allyl alcohol which in turn is subjected to sequential amination and oxidation reactions to yield bio-acrylonitrile.

Catalytic Conversion of 1,3-propanediol into Acrylonitrile with Allyl Alcohol and Allyl Amine as an Intermediate:

In one embodiment of the present invention, a process is provided wherein bio-1,3-propanediol is subjected to a dehydration reaction to produce allyl alcohol as described in detail in the paragraphs above (FIG. 7). In the next step, the allyl alcohol is subjected to amination reaction to obtain allyl amine which is subsequently oxidized to yield acrylonitrile (FIG. 8). Amination of allyl alcohol is achieved by means of contacting allyl alcohol in the presence of an effective amount of ammonia and a phosphorus containing substance at a specified temperature. The temperature suitable for this amination reaction may range from about 0° C. to 400° C., preferably from about 150° C. to 350° C. The catalysts suitable for this amination reaction are disclosed in U.S. Pat. No. 4,036,881, U.S. Pat. No. 3,869,526 and U.S. Pat. No. 3,869,527 which are inculpated herein by reference. European Patent Specification No. 0,078,000 provides details about other experimental conditions for aminating allyl alcohol. These U.S. patents and European Patent document are incorporated herein by reference.

Once bio-allyl amine is obtained, it is subjected to oxidation reaction to produce bio-acrylonitrile. U.S. Pat. No. 3,940,429 and U.S. Pat. No. 3,983,161 provide details about an oxidation process for the conversion of an unsaturated amine to an unsaturated nitrile in which the oxidation reaction takes place in the presence of a nitrogen base, a cuprous halide and an alcoholic compound. These two U.S. Patent documents are incorporated herein by reference.

Figure 9:
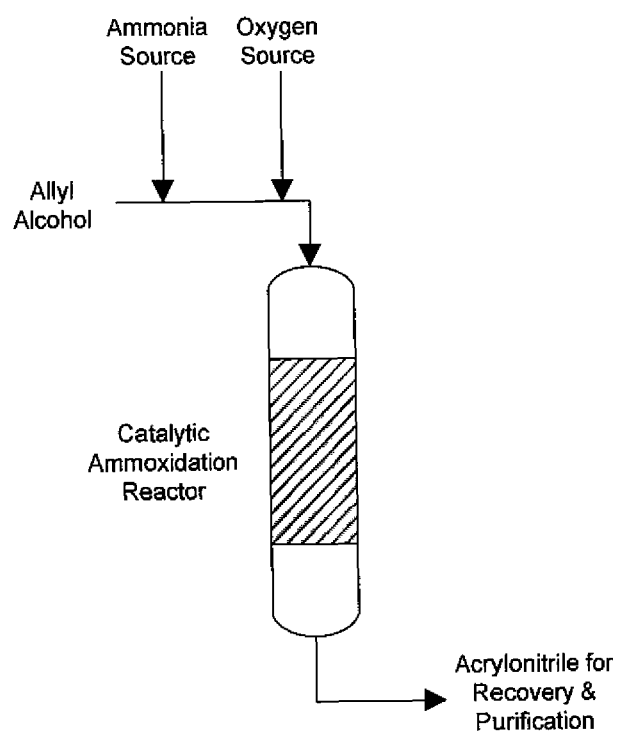
FIG. 9. Simplified process configuration for bio-acrylonitrile production involving single-step amino-oxidation reaction in an ammoxidation reactor. Biomass-derived 1,3-propanediol is subjected to dehydration reaction to yield allyl alcohol which in turn is subjected to combined amination and oxidation reactions in a single step to yield bio-acrylonitrile.

In another aspect of the present invention, the amination and oxidation reactions are carried out in a single step and it is referred as ammoxidation or amino-oxidation reaction (FIG. 9). Ammoxidation catalysts have been disclosed in the U.S. Pat. No. 3,907,859, U.S. Pat. No. 3,962,309, U.S. Pat. No. 3,993,680, U.S. Pat. No. 4,018,712, U.S. Pat. No. 4,263,449 and U.S. Pat. No. 4,405,498. All of these U.S. Patent documents are herein incorporated by reference. Preferred ammoxidation catalysts suitable for the present invention have the formula: $A_aB_bFe_cBi_dC_eMo_fO_z$ wherein A is an alkali metal, alkaline earth metal Ti, In, rare earth metal or mixtures thereof, B is Ni, Co, Mg, or a mixture thereof; and C is phosphorus, arsenic, boron or antimony; and wherein a and e are independently 0-3; b is 0 to 20; c and d are independently 0.1 to 10; f is about 8 to about 16 and x is the number of oxygen required to satisfy the valence requirements of the other elements present. A reprehensive example of an ammoxidation catalyst useful for the present invention contains at least the oxides of Bi and Mo, Te and Mo or mixtures thereof.

With the wealth of information available on the amination reaction involving allyl alcohol and oxidation reaction involving allyl amine, a person skilled in the art of acrylonitrile manufacturing will be able to practice the present invention related to the manufacturing bio-acrylonitrile using bio-1,3-propanediol as a feedstock.

Figure 10:
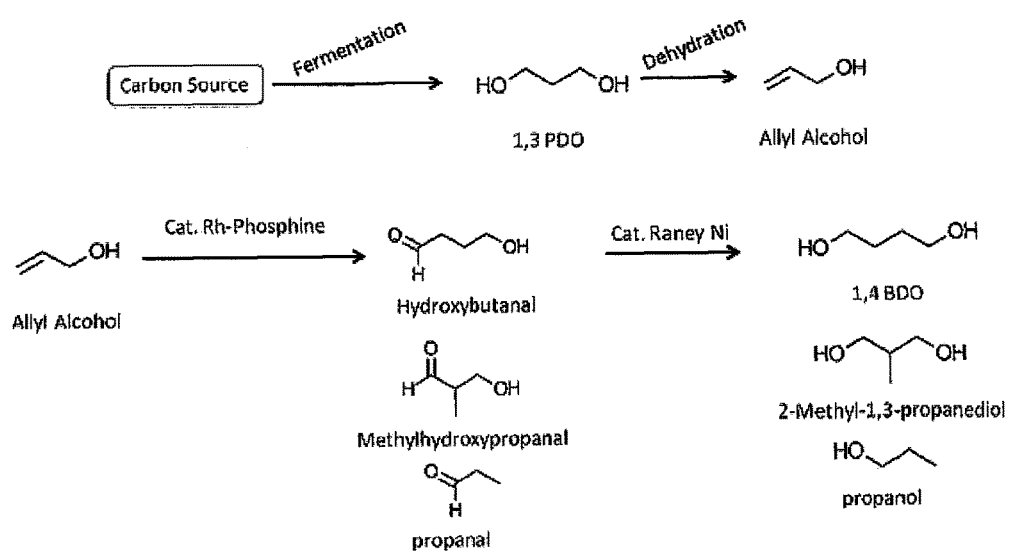
FIG. 10. Bio-1,4-butanediol, bio-2-methyl-1,3-propanediol and bio-n-propanol production from biomass-derived 1,3-propanediol through allyl alcohol intermediate. The 1,3-propanediol useful for the present invention is derived from renewable carbon sources including glucose, sucrose, glycerol and cellulosic hydrolysates through fermentation involving biocatalysts. Biomass-derived 1,3-propanediol is subjected to dehydration reaction to yield bio-allyl alcohol. Upon hydroformylation reaction in the presence of Rh-Phosphine catalyst and [CO/H2] gas mixture, bio-allyl alcohol yields bio-hydroxybutanal, methylhydroxypropanal and propanal which are subjected to a hydrogenation reaction in the presence of Raney Nickel catalyst under hydrogen gas to yield bio-1,4-butanediol, bio-2-methyl-1,3-propanediol and bio-n-propanol.

Catalytic Conversion of 1,3-propanediol into 1,4-butanediol:

FIG. 10 provides a summary of the bio-1,3-propanediol to bio-1,4-butanediol chemistry. In the first step of 1,4-butanediol manufacturing process, 1,3-propanediol is subjected to a dehydration reaction to yield allyl alcohol as described in detail in the paragraphs above. With allyl alcohol as the substrate, a hydroformylation reaction is initiated in the presence of a rhodium catalyst, phosphine and [CO/H2] resulting in the formation of hydroxybutanal (HBA), methylhydroxypropanal (MHPA), propanl (PA) and n-propanol (NPA). In the next stage, HBA, MHBA and NPA are subjected to a hydrogenation reaction in the presence of Raney Nickel catalyst and [H2] to yield 1,4-butanediol (BDO), 2-methyl-1,3-propanediol (MPDiol) and n-propanol (NPA). 2-methyl-1,3-propanediol is a colorless. Low viscosity liquid with a unique molecular structure. It is a branched asymmetric aliphatic diol and inhibits crystallization allowing it remains liquid even in cold temperature.

2-methyl-1,3-propanediol is found in variety of applications, including personal care, coatings, agricultural and cleaners.

Figure 11:
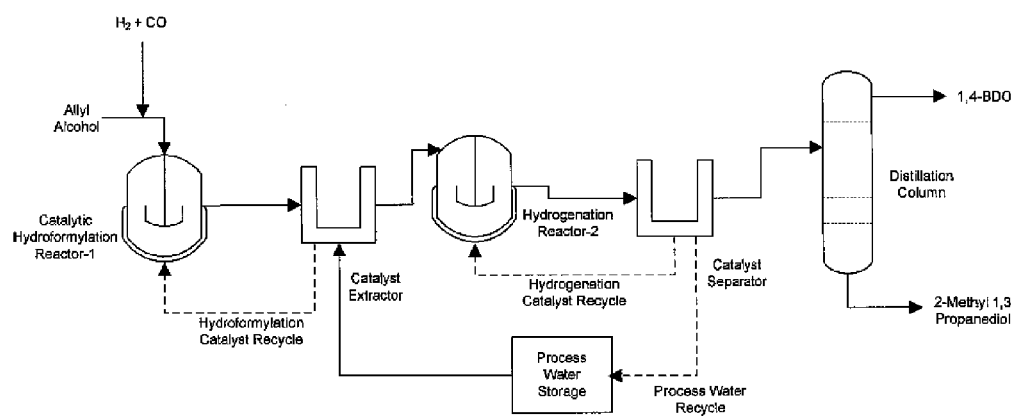
FIG. 11. Simplified process configuration for production of bio-1,4-butanediol and bio-2-methyl-1,3-propanediol. Biomass-derived 1,3-propanediol is subjected to dehydration reaction to yield allyl alcohol which in turn is subjected to hydroformylation and hydrogenation reactions to yield bio-1,4-butanediol and bio-2-methyl-1,3-propanediol.

FIG. 11 provides a simplified process configuration for production of bio-1,4-butanediol and bio-2-methyl-1,3-propanediol. Biomass-derived 1,3-propanediol is subjected to catalytic dehydration reaction to yield allyl alcohol which is fed into a catalytic hydroformylation in Reactor 1. Effluent from Reactor 1 is sent to a Catalyst Extractor where it is mixed with water from Water Storage tank and the hydroformylation catalyst is recovered and recycled. The recovered product effluent stream from Catalyst Extractor is sent to Reactor-2 and subjected to hydrogenation reaction using hydrogenation catalyst. The effluent stream from Reactor-2 is sent to a Catalyst Separator where the hydrogenation catalyst is recovered and recycled while the recovered process water is recycled to the Process Water Storage. The recovered product effluent from Catalyst Separator is sent to a Distillation column to recover 1,4-Butanediol and 2-methyl 1,3-propanediol through fractional distillation.

U.S. Pat. No. 4,465,873 provides a process for obtaining butanediol by distilling the same from an aqueous solution obtained by hydrogenation of a hydroformylated allyl alcohol carried out in the presence of a nickel catalyst, The invention disclosed in this U.S. patent provides a process involving distillation to separate 2-methyl-1,3-propanediol, 1,4-butanediol and a high-boiling fraction from a butanediol mixture obtained from the hydrogenation reaction.

U.S. Pat. No. 4,567,305 provides conditions for hydroformylation of allyl alcohol with a gaseous mixture of hydrogen and carbon monoxide, in an aromatic hydrocarbon, in the presence of a rhodium complex and trisubstituted phosphine to hydroxybutyraldehydes which are separated from the reaction mixture within an aqueous medium. More specifically this U.S. patent provides the way to select and control carbon monoxide partial pressure, the rate of consumption of carbon monoxide, the rate at which the carbon monoxide is dissolved in the reaction mixture, reaction temperature and the viscosity of the reaction mixture to give a high yield of 4-hydroxybutyraldehyde and reduced catalyst consumption.

U.S. Pat. No. 4,529,808 provides a bisolvent system for the hydroformylation of allyl alcohol using a rhodium catalyst. The bisolvent system may comprise materials such as p-xylene and acetamide. Such a bisolvent system provides for easy catalyst recovery since the rhodium catalyst is selectively soluble in the p-xylene whereas the desired product is conversely selectively soluble in the acetamide phase.

U.S. Pat. No. 4,590,311 provides a process for preparation of 1,4-butanediol involving reaction of allyl alcohol with carbon monoxide and hydrogen in the presence of a soluble rhodium catalyst, certain phosphine promoter and certain carbonitriles as solvent.

U.S. Pat. No. 5,290,743 provides a process for regenerating a deactivated hydroformulation catalyst system that contains a rhodium hybridocarbonyl tris(trisubstituted phosphine) complex, a trisubstituted phosphine and a diphosphinoalkane. The process involves oxidation of the catalysts system, removal of the phosphine oxidation products, and regeneration of the catalyst system by syngas treatment, aqueous extraction, and addition of phosphine ligands.

U.S. Pat. No. 5,426,250 provides process in which the hydroformylation product is extracted with an alkaline aqueous solution in the presence of carbon monoxide and/or hydrogen. After the extraction, an extracted raffinate solution containing the rhodium complex in the organic solvent is recycled through the same hydroformylation process while the extracted aqueous solution containing the hydroformylation product is subjected to a hydrogenation reaction in the presence of hydrogen, with a hydrogenation catalyst added, to produce 1,4-butanediol.

U.S. Pat. No. 5,693,832 provides novel phosphine compounds used in the hydroformylation reaction.

U.S. Pat. No. 5,981,810 provides a process for purifying crude 1,4-butanediol by subjecting it to melt crystallization.

U.S. Pat. No. 6,127,584 provided a process in which allyl alcohol is hydroformylated to 1,4-butanediol using a rhodium and trialkyl phosphine catalyst having at least 2 methyl groups, the reaction being carried out at milder conditions and subsequently at more, severe conditions.

U.S. Pat. No. 6,225,509 provides a process for reducing the undesirable make of C3 co-products in a hydroformylation reaction. According to this process, the CO concentration must be maintained above 4.5 mg mols/liter of reaction liquid, preferably above about 5.0 mg·mol/liter in order to achieve high 4-hydroxybutyaldehyde selectivities.

U.S. Pat. No. 6,426,437 provides a process giving high yield of 1,4-butanediol compared to 2-methyl-1,3-propanediol.

U.S. Pat. No. 6,969,780 provides a process for the reduction of hydrogenation catalyst deactivation and deterioration.

U.S. Pat. No. 7,271,295 provides a process comprising a rhodium complex and a 2,3-O-isopropylidene-2,3-dihydroxy-1,4bis[bis(3,5-di-n-alkylphenyl)phosphino]butane. This process gives high yield of 4-hydroxybutyraldehyde compared to 3-hydroxy-a-methylpropionaldehyde.

U.S. Pat. No. 7,279,606 provides a process comprising a rhodium complex and a trans-1,2-bis(bis)3-5-di-n-alkylphenyl)phosphinomethyl)-cyclobutane. This process gives high yield of 4-hydroxybutyraldehyde compared to 3-hydroxy-a-methylpropionaldehyde.

U.S. Pat. No. 6,969,780 provides a process for improving the catalytic hydrogenation of 4-hydroxybutyraldehyde and 2-methyl 3-hydroxypropionaldehyde.

U.S. Patent Application Publication No. 2014/0135537 relates to system and methods for monitoring the feed and effluent streams during the production of 1,4-butanediol using Raman spectroscopy.

All the U.S. patents and the U.S. patent application Publication listed in the paragraphs immediately above are incorporated herein by reference. With these disclosures related to the conversion of allyl alcohol to 1,4-butanediol provided in these patent documents, a person skilled in the art of manufacturing industrial commodity chemicals, particularly 1,4-butanediol will be able to able to carry out the hydroformylation and hydrogenation reactions with bio-allyl alcohol to manufacture bio-1,4-butanediol.

Figure 13:
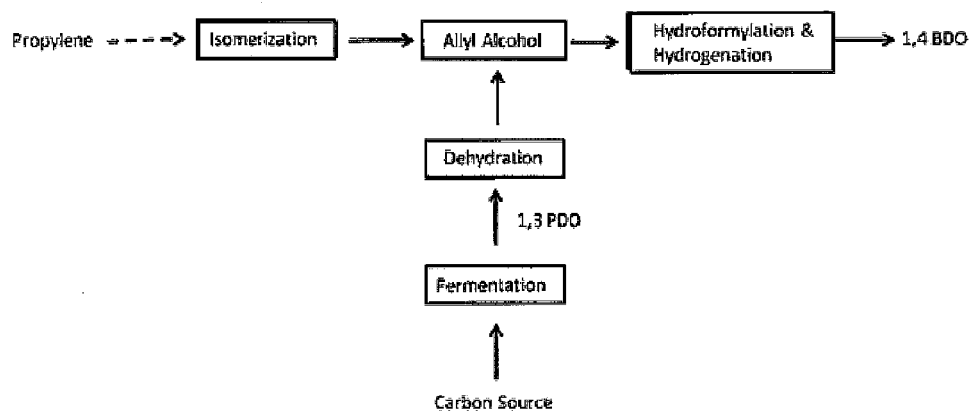
FIG. 13. Use of bio-allyl alcohol as a drop-in chemical in the conventional process for the production of 1,4-butanediol. In the conventional chemical process for the production of 1,4 butanediol, propylene oxide is isomerized to yield allyl alcohol which in turn is subjected to hydroformylation and hydrogenation reactions to yield 1,4-butanediol. In the process according to the present invention, 1,3-propanediol is derived from biomass-derived carbon sources through fermentation process involving biocatalysts. Upon dehydration reaction, biomass-derived 1,3-propanediol yields bio-allyl alcohol which in turn is used as a drop-in chemical in the conventional process for the production of bio-1,4-butanediol.

In an alternative embodiment of the present invention, bio-allyl alcohol can be used as a drop-in chemical intermediate in the conventional BDO plant operated using petrochemical feedstock as provided in the FIG. 13.

The embodiments described above have been provided only for the purpose of illustrating the present invention and should not be treated as limiting the scope of the present invention. The chemical reaction schemes depicted herein are just examples. There may be many variations to these chemical reaction schemes or the steps or operations described therein without departing from the spirit of the invention. Numerous modifications of the embodiments described herein may be readily suggested to one of skilled in the art without departing from the scope of the appended claims. It is intended, therefore, that the appended claims encompass such modifications to the embodiments disclosed herein.

Example 1

Analytical Method

Figure 14:
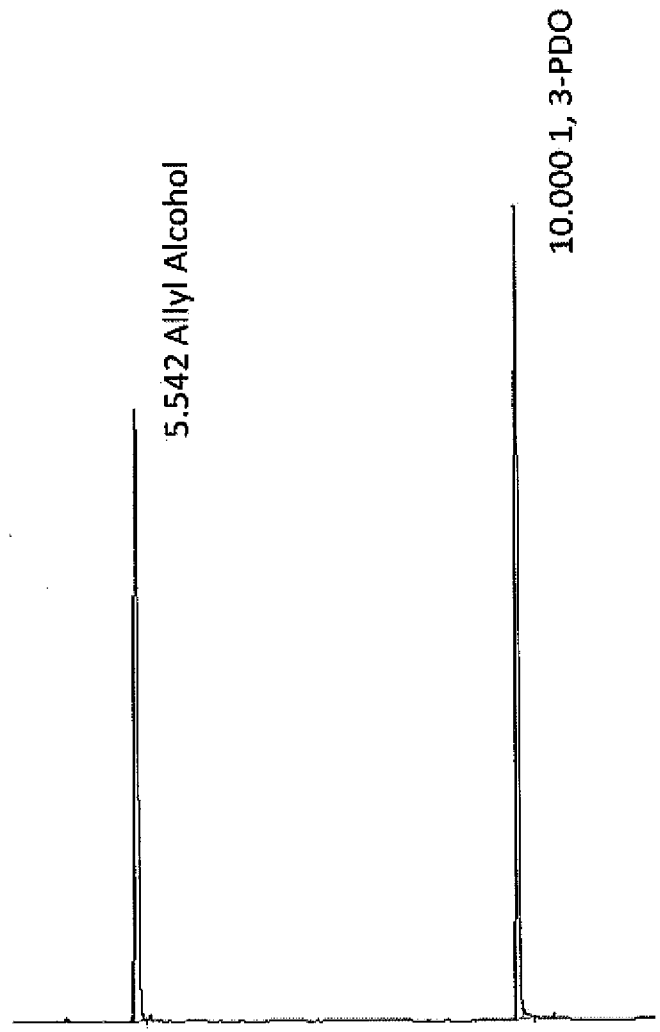
FIG. 14. Elution profile of 1,3-propanediol and allyl alcohol as detected under the HPLC conditions used in the present invention. The allyl alcohol (5.542 minute) and 1,3-propanediol (10.000 minute) peaks were well separated under the experimental conditions described in Example 1.
Figure 15:
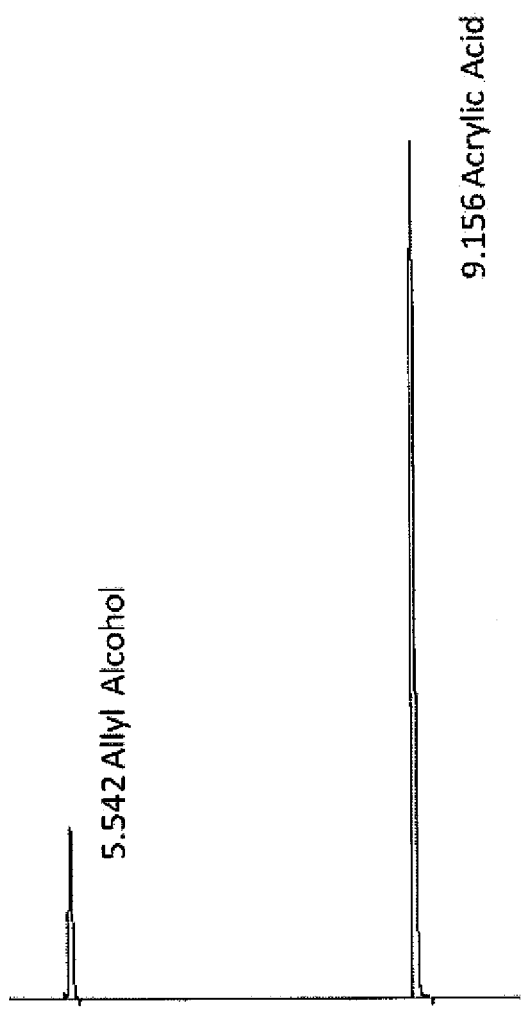
FIG. 15. Elution profile of acrylic acid and allyl alcohol as detected under the HPLC conditions used in the present invention. The allyl alcohol (5.542 minute) and acrylic acid (9.156 minute) peaks were well separated under the experimental conditions described in Example 1.

The dehydration of 1,3-propanediol leading to the formation of ally alcohol as well the oxidation of allyl alcohol leading to the production of acrylic acid were monitored using gas chromatographic (GC) analysis. Agilent 7890A GC equipment was used with Agilent 7683B autosampler. HP-FFAP (25 m×0.32 mm×0.5 µm) column was used. Injector temperature was maintained at 250° C. and operated in split mode 25:1 (37.35 ml/min HE). One microliter sample was injected. FID detector was maintained at 300° C. (44 ml·min H2. 400 ml/min Air, 30 ml/min makeup He). The oven profile was maintained as follows: 40° C. hold for 2 minutes; ramp 20° C./min to 230° C.; hold for 8 minutes. As shown in the FIGS. 14 and 15, under these chromatographic conditions used in the present invention, 1,3-propanediol, allyl alcohol and acrylic acid peaks were well-resolved thereby making it possible to monitor the dehydration and oxidation reactions precisely.

Example 2

Dehydration of 1,3-propanediol

Neat 1,3-propanediol (1.52 gram) and formic acid (10, 20, and 50 molar equivalents with reference to molar concentration of 1,3-propanediol) were added to a clean, dry 50 mL pressure tube at room temperature. The resulting homogeneous mixture was heated at 120° C. for 5 hours. After 5 hours of incubation at 120° C., 0.2 ml of the reaction mixture was withdrawn and dissolved in 1 ml of water. This diluted solution was directly used for GC analysis. As the results shown in Table 1 indicate the conversion efficiency increased proportionally with an increase in the concentration of formic acid. At formic concentration of 50 molar equivalents with reference to molar concentration of 1,3-propanediol, the maximum conversion efficiency of 74% was obtained.

Example 3

Oxidation of Allyl Alcohol to Acrylic Acid

Neat allyl alcohol (1.2 gram) and water (100 mL) were added to a clean, dry 500 mL round bottom flask. The colorless homogenous solution was stirred at room temperature. $KMNO_4$ (2 and 10 molar equivalent with reference to molar concentration of allyl alcohol) was slowly added to the solution at room temperature. A slight rise in temperature was observed. The addition of $KMNO_4$ was controlled in order to maintain the temperature of the flask under 30° C. After the completion of addition of $KMNO_4$, the reaction mixture was stirred at room temperature for 5 hours. At the end of five hours, 0.1 ml solution was withdrawn from the reaction mixture and dissolved in 10 ml of 1% $Na_2SO_3$ in water. 0.1 ml of the diluted solution was further diluted to 1 ml water and directly used for GC analysis. The GC analysis showed that the conversion efficiency increased with an increase in the molar concentration of $KMNO_4$. With 10 molar equivalents of $KMNO_4$ in the oxidation reaction mixture, the efficiency for the conversion of allyl alcohol into acrylic acid was found to be 83% (Table 2)

Example 4

Dehydration of 1,3-propanediol

Neat Bio 1,3-propanediol (PDO, DuPont Tate& Lyle 50 ml) was added to CeO2 (Aldrich, 7.8 g) on a clean 250 ml round bottom flask kept at room temperature. The flask was attached to a short air condenser column followed by a distillation condenser and receiving flask. The contents were heated to 300° C. jacket temperature. PDO started to boil at 250° C. Most of the PDO condensed at the air condenser, but low boiling allyl alcohol condensed at the distillation condenser. Bio-Allyl alcohol was collected at 2 ml an hour rate. The reaction was continued by portion wise addition of PDO (50 ml) for every 12 h. Bio-Allyl alcohol was collected as 50 ml portion was analyzed by GC for purity. Overall yield for allyl alcohol was in the range of 85%-90% and the purity was in the range of 92%-98%.

Example 5

Oxidation of Allyl Alcohol to Acrylic Acid

Neat allyl alcohol (5 mmol, 0.34 g) in Acetone (5 ml) and water (1 mL) was added a solution of CrO3 in H2SO4 (2.3 M, 5.5 ml) at 0° C. slowly over 30 min by keeping the temperature between 0° C. to 10° C. The solution turned to a dark red color. The reaction was maintained at this temperature for over 30 min and a solution of isopropanal was added until the reaction color turned to a light green solution. The solid precipitates were filtered through a pad of Celite and the resulting solution was analyzed through GC for the presence of Acrylic acid. The reaction showed a complete conversion and the selectivity to Acrylic acid was 97%.

REFERENCES

All references are listed for the convenience of the reader. Each reference is incorporated by reference in its entirety.

U.S. Pat. No. 3,775,474
U.S. Pat. No. 3,869,526
U.S. Pat. No. 3,869,527
U.S. Pat. No. 3,893,951
U.S. Pat. No. 3,907,859
U.S. Pat. No. 3,940,429
U.S. Pat. No. 3,954,855
U.S. Pat. No. 3,962,309
U.S. Pat. No. 3,983,161
U.S. Pat. No. 3,993,680
U.S. Pat. No. 4,018,712
U.S. Pat. No. 4,036,881
U.S. Pat. No. 4,051,181
U.S. Pat. No. 4,107,204
U.S. Pat. No. 4,144,398
U.S. Pat. No. 4,339,355
U.S. Pat. No. 4,405,498
U.S. Pat. No. 4,465,873
U.S. Pat. No. 4,529,808
U.S. Pat. No. 4,567,305
U.S. Pat. No. 4,590,311
U.S. Pat. No. 4,871,700
U.S. Pat. No. 5,164,309
U.S. Pat. No. 5,254,467

U.S. Pat. No. 5,290,743
U.S. Pat. No. 5,387,720
U.S. Pat. No. 5,426,250
U.S. Pat. No. 5,633,362
U.S. Pat. No. 5,686,276
U.S. Pat. No. 5,693,832
U.S. Pat. No. 5,821,092
U.S. Pat. No. 5,981,810
U.S. Pat. No. 6,013,494
U.S. Pat. No. 6,127,584
U.S. Pat. No. 6,225,509
U.S. Pat. No. 6,361,983
U.S. Pat. No. 6,426,437
U.S. Pat. No. 6,428,767
U.S. Pat. No. 6,479,716
U.S. Pat. No. 6,514,733
U.S. Pat. No. 6,969,780
U.S. Pat. No. 7,074,608
U.S. Pat. No. 7,135,309
U.S. Pat. No. 7,271,295
U.S. Pat. No. 7,211,692
U.S. Pat. No. 7,223,567
U.S. Pat. No. 7,259,280
U.S. Pat. No. 7,279,606
U.S. Pat. No. 7,371,558
U.S. Pat. No. 7,745,184
U.S. Pat. No. 7,259,280
U.S. Pat. No. 7,371,558
U.S. Pat. No. 7,858,350
U.S. Pat. No. 7,910,771
U.S. Pat. No. 7,947,483
U.S. Pat. No. 8,067,214
U.S. Pat. No. 8,129,156
U.S. Pat. No. 8,129,169
U.S. Pat. No. 8,129,170
U.S. Pat. No. 8,178,327
U.S. Pat. No. 8,252,960
U.S. Pat. No. 8,357,520
U.S. Pat. No. 8,530,210
U.S. Pat. No. 8,597,918
U.S. Pat. No. 8,691,539
U.S. Pat. No. 8,715,971
European Patent Specification No. 0 078 000 B1
U.S. Patent Application Publication No. US20120202259
U.S. Patent Application Publication No. US20120225461
U.S. Patent Application Publication No. US20130130339
U.S. Patent Application Publication No. US20130157328
U.S. Patent Application Publication No. US2014/0135537
International Patent Application Publication No. WO2008/021141A2
International Patent Application Publication No. WO2009/15508A2
International Patent Application Publication No. WO2011/033649A1
International Patent Application Publication No. WO2011/063055A2
International Patent Application Publication No. WO2011/063157A2
International Patent Application Publication No. WO2011/082378A2
International Patent Application Publication No. WO2010/115067A2
International Patent Application Publication No. WO2011/123154A2
International Patent Application Publication No. WO2011/130725A2
International Patent Application Publication No. WO2013/015770A1
International Patent Application Publication No. WO2012/0186995A2
International Patent Application Publication No. WO2012/033845A2
International Patent Application Publication No. WO2012/082720A2
International Patent Application Publication No. WO2013/052717A2
International Patent Application Publication No. WO2013/181255
International Patent Application No. PCT/US13/29368

Burk, M. J. (2010) Sustainable production of industrial chemicals from sugars. *Int. Sugar J.* 112: 30-35.

Da Silva, G. P, Mack, M. and Contiero, J. (2009) Glycerol: A promising and abundant carbon source for industrial microbiology. *Biotech. Adv.* 27: 30-39.

Diaz, E., Sad, M. E., and Iglesia, E. (2010) Homogeneous oxidation reactions of propanediols at low temperatures. *ChemSusChem* 3: 1063-1070.

Drochner, A., Kampe, P., Menning, N., Blickhan, N., Jekewitz, T. and Vogel, H. (2014) Acrolein oxidation to acrylic acid on MON/W-mixed oxide catalysts. *Chem. Eng. Technol.* 37: 398-408.

Gonen, C., Gungormusler, M. and Azbar, N. (2013) Continuous production of 1,3-propanediol using waste glycerol with *Clostridium beijernckii* NRRL B-593 immobilized on glass beads and glass rusing rings. *Chem. Biochem. Eng. Q.* 27: 227-234.

Gum Y., Liu, S., Li, C., and Cui, Q. (2013) Selective conversion of glycerol to acrolein over supported nickel sulfate catalysts. *J. Catalysis,* 301, 93-102.

Industrial Biotechnology Interview (2014) A conversation with Ellen Kullman. *Ind Biotech* 10: 247-250.

Jantama, K., Haupt, M. J., Svoronos, S. A., Zhang, X., Moore, J. C., Shanmugam, K. T., and Ingram, L. O. (2008a) Combining metabolic engineering and metabolic evolution to develop nonrecombinant strains of *Escherichia coli* C that produce succinate and malate. *Biotechnol Bioeng* 99: 1140-1153.

Jantama, K., Zhang, X., Moore, J. C., Shanmugam, K. T., Svoronos, S. A., and Ingram, L. O. (2008) Eliminating side products and increasing succinate yields in engineered strains of *Escherichia coli* C. *Biotechnol Bioeng* 101: 881-893.

McGrew, D. (2010) Getting to the point: Direct bio-based chemical production. *Specialty Chem. Mag.* 30: 32-34.

Mendes, F. S., Gonzalez-Pajuelo, M., Coridier, H., Francois, J. M. and Vasconcelos, I. *App. Microbiol. Biotech.* 92: 519-527.

Nakamura, C. E. and Whited, G. (2003) Metabolic engineering for the microbial production of 1,3-propanediol. *Curr. Opin. Biotech.* 14: 454-459.

Nielson, L. K. (2011) From retrofitting to green field. *Nature Chem. Biol.* 7: 408-409.

Rao, G. S., Pethan Rajan, N., Pavankumar, V., Chary, K. V. R. (2013) Vapor phase dehydration of glycerol to acrolein over NbOPO4 catalysts. *J. Chem. Tech. Biotech.* Published online 17 Dec. 2013.

Raynaud, C., Sarcabal, P., Meyniad-Salles, I., Croux, C. and Soucaille, P. (2003) Molecular characterization of the 1,3-propanediol (1,3-PD) operon of *Clostridium butyicum. Proc. Natl. Acad Sci. USA* 100: 5010-5015.

Sato, S., Takahashi, R., Sodesawa, T., Honda, N. and Shimizu, H. (2003) Selective dehydration of diols to allylic alcohols catalyzed by ceria. *Cata. Comm.* 4: 77-81

Sato, S., Sato, F., Gotoh, H., and Yamada, H. (2013) Selective dehydration of alkanediols into unsaturated alcohols over rare earth oxide catalysts. *ACS Catalysts*. 3: 721-734.

Segawa, M., Sato, S., Kobune, M., Sodesawa, T., Kojima, T., Nishiyama, S. and Ishizawa, N. (2009) Vapor-phase catalytic reactions of alcohols over bixbyite indium oxide. *J. Mol. Cata. A: Chemical* 310, 166-173.

Soriano, M. D., Concepion, P., Nieto, J. M. L., Cavani, F., Guidetti, S., and Trevisanut, C. (2011) Tungsten-vanadium mixed oxides for the oxidehydration of glycerol into a acrylic acid. *Green Chem*. 13: 2954-2962.

Szymanowska-Powalowska, D. and Leja, K. (2014) An increasing of the efficiency of microbiological synthesis of 1,3-propanediol from crude glycerol by the concentration of biomass. *Electronic J. Biotech*. 17:72-78

Tang, X., Tan, Y., Zhu, H., Zhao, K. and Shen, W. (2009) Microbial conversion of glycerol to 1,3-propanediol by an engineered strain of *Escherichia coli*. *App. Env. Microbiol*. 75: 1628-1634.

Tahnsilp, S., Schwank, J. W., Meeyoo, V., Pnegpanich, S., and Hunsom, M. (2013) Preparation f supported POM catalysts for liquid phase oxydehydration of glycerol to acrylic acid. *J. Mol. Catalysts A; Chemical* 380: 49-56.

Ulgen, A. and Hoelderich, W. F. (2011) Conversion of glycerol to acrolein in the presence of WO3/TiO2 catalysts. *App. Catalysis A: General*, 400, 34-38.

Vivier, L. and Duprez, D. (2010) Ceria-based solid catalysts for organic chemistry. *ChemSusChem*, 3: 654-678.

Yim, H., Haselbeck, R., Niu, W., Pujol-Baxley, C., Burgard, A., Boldt, J., Khandurina, J., Trawick, J. D., Osterhout, R. E., Stephen, R., Estadilla, J., Teisan, S., Schreyer, H. B., Andrae, S., Yang, T. H., Lee, Lee, S. Y., Burk, M. J. and Van Dien, S. (2011) Metabolic engineering of *Escherichia coli* for direct production of 1,4-butanediol. *Nature Chem Biol*. 7:445-452.

Zeng, A-P. and Sabra, W. (2011) Microbial production of diols as platform chemicals: Recent progresses. *Curr. Opin. Biotech*. 22: 749-757.

TABLE 1

Production of allyl alcohol from 1,3-propanediol

| Formic Acid | PDO mg/ml | Ally Alcohol mg/ml | Conversion Efficiency |
|---|---|---|---|
| 10 Equ | 15.34 | 8.87 | 43% |
| 20 Equ | 5.37 | 12.91 | 57% |
| 50 Equ | 4.60 | 16.85 | 74% |

TABLE 2

Production of acrylic acid from allyl alcohol

| KMnO4 | Allyl Alcohol mg/ml | Acrylic Acid mg/ml | Conversion Efficiency |
|---|---|---|---|
| 2 Equ | 15.03 | 9.81 | 34% |
| 10 Equ | 3.04 | 18.73 | 83% |

What is claimed:

1. A process for preparing acrylic acid, comprising:
   a. catalytic dehydrating 1,3-propanediol to yield allyl alcohol; and
   b. oxidizing said allyl alcohol to yield acrylic acid using a catalyst, wherein said catalyst is KMnO$_4$ or CrO$_3$ in H$_2$SO$_4$.

2. The process for preparing acrylic acid of as in claim 1, wherein the 1,3-propanediol is obtained from biomass through a fermentative process.

3. A process for preparing acrylic acid, comprising:
   a. catalytic dehydrating 1,3-propanediol using a catalyst to yield a mixture of allyl alcohol and acrolein, wherein said catalyst is selected from the group consisting of NbOPO$_4$, WO$_3$/TiO$_2$; and
   b. oxidizing said mixture of allyl alcohol and acrolein to yield acrylic acid using a catalyst, wherein said catalyst is KMnO$_4$ or CrO$_3$ in H$_2$SO$_4$.

4. The process for preparing acrylic acid of claim 3, wherein the 1,3-propanediol is obtained from biomass through a fermentative process.

* * * * *